US009254318B2

(12) United States Patent
Kawaoka et al.

(10) Patent No.: US 9,254,318 B2
(45) Date of Patent: Feb. 9, 2016

(54) HIGH TITER RECOMBINANT INFLUENZA VIRUSES FOR VACCINES

(75) Inventors: Yoshihiro Kawaoka, Middleton, WI (US); Taisuke Horimoto, Madison, WI (US); Shin Murakami, Tokyo (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/729,557

(22) Filed: Mar. 29, 2007

(65) Prior Publication Data

US 2007/0231348 A1    Oct. 4, 2007

(51) Int. Cl.
| A61K 39/12 | (2006.01) |
| A61K 39/145 | (2006.01) |
| C12N 7/00 | (2006.01) |
| C12N 15/85 | (2006.01) |
| A61K 39/00 | (2006.01) |

(52) U.S. Cl.
CPC .............. *A61K 39/145* (2013.01); *A61K 39/12* (2013.01); *C12N 7/00* (2013.01); *C12N 15/85* (2013.01); *A61K 2039/525* (2013.01); *A61K 2039/5254* (2013.01); *C12N 2760/16051* (2013.01); *C12N 2760/16134* (2013.01); *C12N 2760/16151* (2013.01); *C12N 2800/107* (2013.01)

(58) Field of Classification Search
None
See application file for complete search history.

(56) References Cited

U.S. PATENT DOCUMENTS

| 6,544,785 | B1 | 4/2003 | Palese et al. | |
| 7,037,707 | B2 * | 5/2006 | Webster et al. | ............ 435/235.1 |
| 7,226,774 | B2 | 6/2007 | Kawaoka | |
| 7,507,411 | B2 * | 3/2009 | Zhou et al. | ................. 424/186.1 |
| 8,012,736 | B2 | 9/2011 | Hoffman et al. | |
| 8,309,099 | B2 | 11/2012 | Hoffmann | |
| 8,475,806 | B2 | 7/2013 | Kawaoka | |
| 2002/0164770 | A1 | 11/2002 | Hoffmann | |
| 2003/0035814 | A1 | 2/2003 | Kawaoka et al. | |
| 2007/0231348 | A1 * | 10/2007 | Kawaoka et al. | .......... 424/209.1 |
| 2012/0020997 | A1 | 1/2012 | Hoffman et al. | |

FOREIGN PATENT DOCUMENTS

| AU | 2012204138 | B2 | 5/2014 |
| EP | 1201760 | A1 | 5/2002 |
| EP | 2010557 | B1 | 2/2014 |
| JP | 2004-500842 | A | 1/2004 |
| JP | 2005-523698 | A | 8/2005 |
| JP | 2005-245302 | A | 9/2005 |
| JP | 2005-535288 | A | 11/2005 |
| JP | 2014131516 | A | 7/2014 |
| WO | WO-00/60050 | A2 | 10/2000 |
| WO | WO-01/83794 | A2 | 11/2001 |
| WO | WO-03/068923 | A2 | 8/2003 |
| WO | WO-03/091401 | A2 | 11/2003 |
| WO | WO-2004/112831 | A2 | 12/2004 |
| WO | WO-2004/112831 | A2 | 7/2005 |
| WO | WO-2005/062820 | A2 | 7/2005 |
| WO | WO-2007/126810 | A2 | 11/2007 |

OTHER PUBLICATIONS

Voeten et al., Characterization of high-growth reassortant infuenza A virus generated in MDCK cells cultured in serum-free medium, 1999, Vaccine, vol. 17, pp. 1942-1950.*
Kiseleva et al., Role of individual genes of the A/Leningrad/134/17/57 (H2N2) cold-adapted donor strain in manifestation of the temperature-sensitive phenotype of reassortant influenza A viruses, 2004, International Congress Series, vol. 1263, pp. 547-550.*
Lee et al., Generation of reassortant influenza vaccines by reverse genetics that allows utilization of a DIVA (Differentiating Infected from Vaccinated Animals) strategy for the control of avian influenza, 2004, Vaccine, vol. 22, pp. 3175-3181.*
Muster et al., An influenza A virus containing influenza B virus 5' and 3' noncoding regions on the neuraminidase gene is attenuated in mice, 1991, PNAS, vol. 88, pp. 5177-7181.*
Verma et al., Gene therapy—promises, problems and prospects, 1997, Nature, vol. 389, pp. 239-242.*
Orkin et al., Report and Recommendations of the Panel to Assess the NIH Investment in Research on Gene Therapy, 1995, downloaded on Sep. 5, 2008 from <http://www.nih.gov/news/panelrep.html>.*
Matsuoka et al., Neuraminidase Stalk Length and Additional Glycosylation of the Hemagglutinin Influence the Virulence of Influenza H5N1 Viruses for Mice, 2009, Journal of Virology, vol. 83, No. 9, pp. 4704-4708.*
Lazarovits et al., Endocytosis of Chimeric Influenza Virus Hemagglutinin Proteins That Lack a Cytoplasmic Recognition Feature for Coated Pits, 1996, The Journal of Cell Biology, vol. 134, No. 2, pp. 339-348.*
Yannarell et al., Factors affecting the yield of cold-adapted influenza virus vaccine, 1997, Journal of Virological Methods, vol. 64, pp. 161-169.*
Results 1, NCBI Blast nucleotide search of SEQ ID No. 7, database "nr"; Result 1, NCBI Blast nucleotide search of SEQ ID No. 8, database "Jul. 23, 2006", (Jul. 23, 2006), 8 pgs.
Result 17, NCBI Blast nucleotide search of SEQ ID No. 2, database "nr", (Jul. 18, 2006), 3 pgs.
Result 7, NCBI Blast nucleotide search of SEQ ID No. 1, database "nr", (Jul. 18, 2006), 3 pgs.
Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

(Continued)

*Primary Examiner* — Benjamin P Blumel
(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes at least five internal genes from an influenza virus isolate that replicates to high titers in embryonated chicken eggs or MDCK cells.

32 Claims, 17 Drawing Sheets

(56) References Cited

OTHER PUBLICATIONS

Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

PCT Application No. PCT/US2004/016680, International Search Report mailed Feb. 2, 2005, 7 pgs.

"PCT Application No. PCT/US2007/007562, International Search Report mailed Jan. 14, 2008", 8 pgs.

"PCT Application No. PCT/US2007/007562, Written Opinion mailed Jan. 14, 2008", 9 pgs.

De, B. P., et al., "Reverse Genetics of Negative Strand RNA Viruses", *Indian Journal of Biochemistry & Biophysics*, 31, (1994), 367-375.

Dreher, T. W., et al., "Mutational Analysis of the Sequence and Structural Requirements in Brome Mosaic Virus RNA for Minus Strand Promoter Activity", *Journal of Molecular Biology*, 201(1), (1988), 31-40.

Elliott, R. M., et al., "Rescue of Infectious Bunyavirus Entirely From Cloned cDNA", *10th International Conference on Negative Strand Virus*, (Abstract No. 96), (1997), 1 pg.

Fodor, E., "Rescue of Influenza A Virus from Recombinant DNA", *Journal of Virology*, 73(11), (1999), 9679-9682

Hoffmann, E., et al., "Ambisense Approach for the Generation of Influenza A Virus: vRNA and mRNA Synthesis from One Template", Virology, 267, (2000), 310-317.

Hoffmann, E., et al., "A DNA Transfection System for Generation of Influenza A Virus from Eight Plasmids", *Proceedings of the National Academy of Sciences of USA, National Academy of Science*, 97(11), (2000), 6108-6113.

Hoffmann, E., et al., "Eight-plasmid System for Rapid Generation of Influenza Virus Vaccines", *Vaccine, Butterworth Scientific Guildford*, 20(25-56), (2002), 3165-3170.

Hoffmann, E., et al., "Rescue of Influenza B Virus from Eight Plasmids", *Proceedings of the National Academy of Sciences of USA, National Academy of Science*, 99(17), (2002), 11411-11416.

Holmes, E. C., et al., "Whole-Genome Analysis of Human Influenza A Virus Reveals Multiple Persistent Lineages and Reassortment Among Recent H3N2 Viruses", *PLoS Biology*, 3(9), (2005), 1579-1589.

Horimoto, T., et al., "Generation of Influenza A Viruses with Chimeric (Type A/B) Hemagglutinins", *Journal of Virology*, 77(14), (2003), 8031-8038.

Horimoto, T., et al., "The Development and Characterization of H5 Influenza Virus Vaccines Derived from a 2003 Human Isolate", *Vaccine*, 24(17), (2006), 3669-3676.

Katinger, D., et al., "Attenuated Influenza Viruses as a Vector for Mucosal Immunization Against HIV-1", *Vaccines*, 97, Cold Spring Harbor,(1997), 315-319.

Lamb, R. A., et al., "Chapter 20—*Paramyxoviridae*: The Viruses and Their Replication", *In: Fundamental Virology*, Fields, B. N., et al., Editors, Lippincott-Raven (2nd Edition),(1996), 577-647.

Neumann, G., et al., "Generation of influenza A Virus from Cloned cDNAs—Historical Perspective and Outlook for the New Millenium", *Reviews in Medical Virology*, 12(1), (2002), 13-30.

Neumann, G., et al., "Generation of Influenza A Viruses Entirely from Cloned cDNAs", *Proc. Natl. Acad. Sci. USA*, 96(16), (1999), 9345-9350.

Neumann, G., et al., "Plasmid-Driven Formation of Influenza Viruslike Particles", *Journal of Virology, The American Society For Microbiology*, 74(1), (2000), 547-551.

Odagiri, T., et al., "Nucleotide Sequence of the PA Gene of Influenza A/WSN/33 (H1N1)", *Nucleic Acids Research*, 18(3), Department of Virology, (1990), p. 654.

Schickli, J. H., et al., "Plasmid-only Rescue of Influenza A Virus Vaccine Candidates", *Philosophical Transactions of the Royal Society of London. Series B, Biological Sciences*, 356(1416), (2001), 1965-1973.

Smeenk, et al., "Mutations in the Hemagglutinin and Matrix Genes of a Virulent Influenza Virus Variant, A/FM/1/47-MA, Control Different Stages in Pathogenesis", *Virus Research 44*, (1996) ,79-95.

Subbarao, K., et al., "Evaluation of a Genetically Modified Reassortant H5N1 Influenza A Virus Vaccine Candidate Generated by Plasmid-based Reverse Genetics", *Virology*, vol. 30(1), (2003), 192-200.

"European Application Serial No. 07754132.4, Office Action mailed Apr. 28, 2009", 4 pgs.

"Australian Application Serial No. 2007245192, Office Action mailed Aug. 25, 2011", 2 pgs.

"Chinese Application Serial No. 200780020095.1, First Office Action mailed Jun. 24, 2011", (w/ English Translation), 13 pgs.

"European Application Serial No. 07754132.4, Office Action mailed Sep. 5, 2011", 5 pgs.

"European Application Serial No. 07754132.4, Response filed Feb. 5, 2010 to Office Action mailed Apr. 28, 2009", 15 pgs.

"Australian Application Serial No. 2007245192, Response filed Feb. 28, 2012 to Office Action mailed Aug. 25, 2011", 22 pgs.

"Chinese Application Serial No. 200780020095.1, Office Action mailed May 3, 2012", With English Translation, 10 pgs.

"Chinese Application Serial No. 200780020095.1, Response filed Sep. 17, 2012 to Office Action mailed May 3, 2012", (w/ English Translation of Claims), 17 pgs.

"Chinese Application Serial No. 200780020095.1, Response filed Nov. 8, 2011 to Office Action mailed Jun. 24, 2011", (w/ English Translation of Amended Claims), 20 pgs.

"European Application Serial No. 07754132.4, Office Action mailed Nov. 2, 2012", 4 pgs.

"European Application Serial No. 07754132.4, Response filed Mar. 15, 2012 to Office Action mailed Sep. 5, 2011", 21 pgs.

"Japanese Application Serial No. 2009-502945, Office Action mailed Oct. 23, 2012", (w/ English Translation), 16 pgs.

Chen, H, et ai., "Generation and evaluation of a high-growth reassortant H9N2 influenza A virus as a pandemic vaccine candidate", *Vaccine*, 21(17-18), (May 16, 2003), 1974-1979.

"Australian Application Serial No. 2012204138, First Examiner Report mailed Jul. 16, 2013", 4 pgs.

"Canadian Application Serial No. 2,647,985, Office Action mailed May 15, 2013", 3 pgs.

"Chinese Application Serial No. 200780020095.1, Decision on Rejection mailed Jul. 22, 2013", (w/ English Translation), 11 pgs.

"Chinese Application Serial No. 200780020095.1, Response filed Jun. 9, 2013 to Office Action mailed Jun. 29, 2013", (w/ English Translation of Claims), 10 pgs.

"Australian Application Serial No. 2012204138, Response filed Dec. 24, 2013 to First Examiner Report mailed Jul. 16, 2013", 21 pgs.

"Canadian Application Serial No. 2,647,985 , Response filed Sep. 30, 2013 Office Action mailed May 15, 2013", 20 pgs.

"Chinese Application Serial No. 200780020095.1, Response filed Nov. 5, 2013 to to Decision on Rejection mailed Jul. 22, 2013", (w/ English Translation of Claims), 12 pgs.

"European Application Serial No. 07754132.4, Response filed Jun. 26, 2013", 8 pgs.

"Japanese Application Serial No. 2009-502945, Examiners Decision of Final Refusal mailed Nov. 12, 2013", (w/ English Translation), 8 pgs.

"PCT Application Serial No. PCT/US2007/007562, International Preliminary Report on Patentability mailed Oct. 9, 2008", 5 pgs.

"Chinese Application Serial No. 200780020095.1, Office Action mailed Jan. 29, 2013", (w/ English Translation), 10 pgs.

"European Application Serial No. 07754132.4, Response filed May 10, 2013 to Office Action mailed Nov. 2, 2012", 14 pgs.

"Japanese Application Serial No. 2009-502945, Response filed Apr. 10, 2013 to Office Action mailed Oct. 23, 2012", (w/ English Translation of Claims), 18 pgs.

"Chinese Application Serial No. 200780020095.1, Office Action mailed Mar. 5, 2015", (w/ English Translation), 12 pgs.

"Chinese Application Serial No. 2007800200951, Response filed Jun. 23, 2015 to Office Action mailed Mar. 5, 2015", (w/ English Translation of Claims), 16 pgs.

"Japanese Application Serial No. 2014-049025, Office Action mailed Jun. 16, 2015", (w/ English Translation), 6 pgs.

Baez, M., et al., "Complete nucleotide sequence of the influenza A/PR/8/34 virus NS gene and comparison with the NS genes of the

(56) References Cited

OTHER PUBLICATIONS

A/Udorn/72 and A/FPV/Rostock/34 strains", *Nucleic Acids Research*, 23(8), (1980), 5845-5858.

Winter, G., et al., "The use of synthetic oligodeoxynucleotide primers in cloning and sequencing segment 8 of influenza virus (A/PR/8/34)", *Nucleic Acids Research*, 9(2), (1981), 237-245.

* cited by examiner

A/PR/8/34 (H1N1)

$10^{10}$ EID$_{50}$/ml
HA titer: 1:8,000

$10^{10}$ EID$_{50}$/ml
HA titer: 1:3,200

GROWTH OF REASSORTANT H5N1 VIRUSES POSSESSING PR8(UW)
OR PR8(CAMBRIDGE) INTERNAL GENES IN CHICKEN EMBRYONATED EGGS

| | PA | PB1 | PB2 | HA | NP | NA | M | NS | $LOG_{10}EID_{50}/ml$ |
|---|---|---|---|---|---|---|---|---|---|
| PR8(UW)/1194 | R | R | R | G | R | G | R | R | 9.07 ± 0.37 |
| PR8(UW)/1194-CamPA | B | R | R | G | R | G | R | R | 8.88 ± 0.25 |
| PR8(UW)/1194-CamPB1 | R | B | R | G | R | G | R | R | 9.08 ± 0.38 |
| PR8(UW)/1194-CamPB2 | R | R | B | G | R | G | R | R | 9.05 ± 0.40 |
| PR8(UW)/1194-CamNP | R | R | R | G | B | G | R | R | 9.00 ± 0.20 |
| PR8(UW)/1194-CamPB12 | R | B | B | G | R | G | R | R | 8.75 ± 0.25 |
| PR8(UW)/1194-CamP3 | B | B | B | G | R | G | R | R | 8.56 ± 0.13* |
| PR8(UW)/1194-CamP3NP | B | B | B | G | B | G | R | R | 8.19 ± 0.31* |
| NIBRG-14 | B | B | B | G | B | G | B | B | 8.32 ± 0.20* |

| R | B | G |
|---|---|---|
| PR8(UW) | PR8(CAMBRIDGE) | A/VIETNAM/1194/2004 |

THE EFFECT OF THE M AND NS GENES ON THE GROWTH OF VIRUSES IN CHICKEN EMBRYONATED EGGS

| | PA | PB1 | PB2 | HA | NP | NA | M | NS | ×10⁸ PFU/ml |
|---|---|---|---|---|---|---|---|---|---|
| PR8(UW)/1194 | R | R | R | G | R | G | R | R | 3.39 ± 1.42 |
| PR8(UW)/1194-CamM | R | R | R | G | R | G | B | R | 2.94 ± 0.28 |
| PR8(UW)/1194-CamNS | R | R | R | G | R | G | R | B | 6.25 ± 1.44* |
| NIBRG-14 | B | B | B | G | B | G | B | B | 0.73 ± 0.43 |

R = PR8(UW)   B = PR8(CAMBRIDGE)   G = A/VIETNAM/1194/2004

GROWTH RATES IN MDCK CELL OF REASSORTANTS WITH DIFFERENT HA, NA, AND NS GENES

| | PA | PB1 | PB2 | HA | NP | NA | M | NS | x10⁸ PFU/ml |
|---|---|---|---|---|---|---|---|---|---|
| PR8(UW)/1194 | R | R | R | G1 | R | G1 | R | R | 0.39 ± 0.21 |
| PR8(UW)/1203 | R | R | R | G2 | R | G2 | R | R | 0.40 ± 0.20 |
| PR8(UW)/1203/03FILL | R | R | R | G2 | R | Y | R | R | 1.26 ± 0.47* |
| PR8(UW)/1203/HK213 | R | R | R | G2 | R | BR | R | R | 1.10 ± 0.37* |
| PR8(UW)/1203/03FILL-CamNS | R | R | R | G2 | R | Y | R | B | 2.33 ± 0.27** |
| PR8(UW)/1203/HK213-CamNS | R | R | R | G2 | R | BR | R

FIG. 13

Growth in MDCK cells of the H5N1 vaccine seed virus containing an heterologous NS segment PR8(UW)/1194
Plaque size 1.17mm
Virus titer 4.8 × 10⁷ PFU/ml PR8(UW)/1194 with PR8 (Cambridge) NS
1.83mm ($p < 0.001$)
1.50 × 10⁸ (PFU/ml)

PR8(UW)/1194 with the NS1 K55E mutation
2.49mm ($p < 0.001$)
1.35 × 10⁸ (PFU/ml)

THE GENOTYPE OF AN H5N1 VACCINE SEED VIRUS WITH
HIGH GROWTH CAPACITY IN CHICKEN EMBRYONATED EGGS OR MDCK CELLS

HA: Y — DERIVED FROM A CIRCULATING H5N1 VIRUS, WHOSE CLEAVAGE SITE SEQUENCE WAS ALTERED TO AN AVIRULENT TYPE

NA: BR — DERIVED FROM PR8 FOR PROPAGATION IN EGGS OR DERIVED FROM HK213 FOR PROPAGATION IN MDCK CELLS

OTHERS: R — PB2, PB1, PA, NP, M: DERIVED FROM PR8(UW)

NS: B — DERIVED FROM PR8 (CAMBRIDGE) OR PR8(UW) NS WITH K55E

FIG. 14

PR8(Cambridge)

PB2

AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGACTGAGAATTAGCTCATCCTTCAGTTTTGGTGGA
TTCACATTTAAGAGAACAAGCGGATCATCAGTCAAGAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGGAGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACAGTGGGTTTTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGGACTCTAGCTACTTACTGACAGC
CAGACAGCGACCAAAAGAATTCGGATGGCCATCAATTAGTGTCGAATAGTTTAAAAACGACCTTGTTTCTACT

SEQ ID NO. 33

PB1

AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTGAA
AACTCGTGTATTGAAACGATGGAGGTTGTTCAGCAAACACGAGTAGAACAAGCTGACAACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACATAGGTTAAAAGGAAACAGAGATTGAACAAAAGGGGT
TATCTAATTAGAGCATTGACCCTGAACACAATGACCAAAGATGCTGAGAGGGAAGCTAAAACGGAGAGCAATTGCAACCCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAAGCAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAGATTGCTAACATTGCTCCAATAATGTTCTCAAACAAAATGGCCGAGACTGGGGAAAAGGGTATATG
TTTGAGAGCAAGAGTATGAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCCAATCATGAAGGGATTCAAGCCGGACGTCGACAGGTTTTATCGA
ACCTGTAAGCTACTTGGAATCAATATGAGCAAGAAAAGTCTTACATAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACTGTGG
GAGCAAACCCGTTCCAAAGCTGGACTGCTGGTCTCCGGAGGGCCCAAATTTATCAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAGAAGAGTTCACTGAGATCATGAAGATCTGTTCC
ACCATTGAAGAGCTCAGACGGCAAAAATAGTGAATTTAGCTTGTCCTTCATGAAAAAAATGCCTTGTTTCTACT

SEQ ID NO. 34

FIG. 15A

PR8(Cambridge)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTCGTGGGGAAGAAATGGCCACAAGGGCCGAC
TACACTCTCGATGAAGAAAGCAGGGCTAGGATCAAAACCAGGCTATTCACCATAAGCAAGAAATGGCCAGCAGAGGCCTCTGG
GATTCCTTTCGTCAGTCCGAGAGAGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAGGTAGACTTTGACGACTGT
AAAGATGTAGGTGATTTGAAGCAATATGAGTAGTATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAAGTACTGTGTTCTTGAGATAGGAGATATGCTTCTAAGAAGT
GCCATAGGCCAGGTTTCAAGGCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAACCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGCTATATGAAGCAATTGAGGAG
TGCCTAATTAATGATCCCTGGGTTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT

SEQ ID NO. 35

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGATGCAACGGCTGGTCTGACTCACATGATGATCTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGTCTGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTCTAGCACGGTCTGCACTCATA
TTGAGAGGGTCGGTTGCTCACAAGTCCTGCCTGCCTGCCTGTGTATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCACTAGAGGAGTTCAAATTGCTTCCAATGAAAATATGGAGACTATGGAATCAAGT
ACACTTGAACTGAGAAGCAGGTACTGGGCCATAAGGACCAGAAGTGGAGGAAACACCAATCAACAGAGGGCATCTGCGGGCCAA
ATCAGCATACAACCTTCTCAGTACAGAGAAATCTCCCTTTTTGACAGAACAACCGTTATGGCAGCATTCACTGGGAATACA
GAGGGGAGAACATCTGACATGAGGACCGAAATCATAAGGATGATGGAAAGTGCAAGACCAAGAATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT

SEQ ID NO. 36

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG

FIG. 15B

PR8 (Cambridge)
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT

SEQ ID NO. 37

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAACAGAAAGTGGCAGGCCCTCTTTGTATCAGAATGGACCAGGCGATCATGGATAAAAACATCATACTGAAAG
CGAACTTCAGTGTGATTTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTTGAGCAAATAACATTTATGCAAGCCTTACATCTATTGCTTGAAGTGGAGCAAGAGATAAGA
ACTTTCTCATTTCAGCTTATTTAATAATAAAAAAACACCCTTGTTTCTACT

SEQ ID NO. 38

FIG. 15C

SEQUENCE LISTING

```
<160> NUMBER OF SEQ ID NOS: 38

<210> SEQ ID NO 1
<211> LENGTH: 2233
<212> TYPE: DNA
<213> ORGANISM: Influenza A

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gattcatcga aattggagta acaaggagag aagttcacat atactatctg     420
gaaaaggcca ataaaattaa atctgagaaa acacacatcc acatttttctc gttcactggg     480 gaagaaatgg ccacaaaggc agactacact ctcgatgaag aaagcagggc taggatcaaa     540
accagactat tcaccataag acaagaaatg gccagcagag gcctctggga ttcctttcgt     600
cagtccgaga gaggagaaga gacaattgaa gaaaggtttg aaatcacagg aacaatgcgc     660
aagcttgccg accaaagtct cccgccgaac ttctccagcc ttgaaaattt tagagcctat     720
gtggatggat tcgaaccgaa cggctacatt gagggcaagc tgtctcaaat gtccaaagaa     780
gtaaatgcta gaattgaacc tttttgaaa acaacaccac gaccacttag acttccgaat     840
gggcctccct gttctcagcg gtccaaattc ctgctgatgg atgccttaaa attaagcatt     900
gaggacccaa gtcatgaagg agagggaata ccgctatatg atgcaatcaa atgcatgaga     960
acattctttg gatggaagga acccaatgtt gttaaaccac acgaaaaggg aataaatcca    1020
aattatcttc tgtcatggaa gcaagtactg gcagaactgc aggacattga gaatgaggag    1080
aaaattccaa agactaaaaa tatgaagaaa acaagtcagc taaagtgggc acttggtgag    1140
```

-continued

```
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag gagatatgct tataagaagt   1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttggggggc tatatgaagc aattgaggag   2100
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

```
<210> SEQ ID NO 2
<211> LENGTH: 2341
<212> TYPE: DNA
<213> ORGANISM: Influenza A

<400> SEQUENCE: 2
```

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaacacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca aagaagaaat ggggatcaca actcattttc agagaaagag acgggtgaga    600
gacaatatga ctaagaaaat gataacacag agaacaatgg gtaaaaagaa gcagagattg    660
aacaaaagga gttatctaat tagagcattg accctgaaca caatgaccaa agatgctgag    720
agagggaagc taaaacggag agcaattgca accccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata acaccaaatg gaacgaaaat    960
cagaatcctc ggatgttttt ggccatgatc acatatatga ccagaaatca gcccgaatgg   1020
```

```
ttcagaaatg ttctaagtat tgctccaata atgttctcaa acaaaatggc gagactggga      1080
aaagggtata tgtttgagag caagagtatg aaacttagaa ctcaaatacc tgcagaaatg      1140
ctagcaagca tcgatttgaa atatttcaat gattcaacaa gaaagaagat tgaaaaaatc      1200
cgaccgctct taatagaggg gactgcatca ttgagccctg aatgatgat gggcatgttc       1260 aatatgttaa gcactgtatt aggcgtctcc atcctgaatc ttggacaaaa gagatacacc      1320
aagactactt actggtggga tggtcttcaa tcctctgacg attttgctct gattgtgaat      1380
gcacccaatc atgaagggat tcaagccgga gtcgacaggt tttatcgaac ctgtaagcta      1440
cttggaatca atatgagcaa gaaaaagtct tacataaaca gaacaggtac atttgaattc      1500
acaagttttt tctatcgtta tgggtttgtt gccaatttca gcatggagct tcccagtttt      1560
ggggtgtctg ggatcaacga gtcagcggac atgagtattg gagttactgt catcaaaaac      1620
aatatgataa acaatgatct tggtccagca acagctcaaa tggcccttca gttgttcatc      1680
aaagattaca ggtacacgta ccgatgccat ataggtgaca cacaaatcac aacccgaaga      1740
tcatttgaaa taagaaact gtgggagcaa accgttcca aagctggact gctggtctcc         1800
gacggaggcc caaatttata caacattaga aatctccaca ttcctgaagt ctgcctaaaa      1860
tgggaattga tggatgagga ttaccagggg cgtttatgca cccactgaa cccatttgtc        1920 agccataaag aaattgaatc aatgaacaat gcagtgatga tgccagcaca tggtccagcc     1980
aaaaacatgg agtatgatgc tgttgcaaca acacactcct ggatcccaa aagaaatcga       2040 tccatcttga atacaagtca agaggagta cttgaggatg aacaaatgta ccaaaggtgc         2100
tgcaatttat ttgaaaaatt cttccccagc agttcataca gaagaccagt cgggatatcc      2160
agtatggtgg aggctatggt ttccagagcc cgaattgatg cacggattga tttcgaatct      2220
ggaaggataa agaaagaaga gttcactgag atcatgaaga tctgttccac cattgaagag     2280
ctcagacggc aaaaatagtg aatttagctt gtccttcatg aaaaaatgcc ttgtttctac       2340
t                                                                     2341
```

<210> SEQ ID NO 3
<211> LENGTH: 2341
<212> TYPE: DNA
<213> ORGANISM: Influenza A

<400> SEQUENCE: 3

```
agcgaaagca ggtcaattat attcaatatg gaaagaataa agaactacg aaatctaatg        60 tcgcagtctc gcacccgcga gatactcaca aaaccaccg tggaccatat ggccataatc         120
aagaagtaca catcaggaag acaggagaag aacccagcac ttaggatgaa atggatgatg      180
gcaatgaaat atccaattac agcagacaag aggataacgg aaatgattcc tgagagaaat      240
gagcaaggac aaactttatg gagtaaaatg aatgatgccg atcagaccg agtgatggta         300 tcacctctgg ctgtgacatg gtggaatagg aatggaccaa taacaaatac agttcattat     360
ccaaaaatct acaaaactta ttttgaaaga gtcgaaaggc taaagcatgg aacctttggc      420
cctgtccatt ttagaaacca agtcaaaata cgtcggagag ttgacataaa tcctggtcat      480
gcagatctca gtgccaagga ggcacaggat gtaatcatga agttgttttt ccctaacgaa     540
gtgggagcca ggatactaac atcggaatcg caactaacga taaccaaaga gaagaaagaa       600
gaactccagg attgcaaaat ttctcctttg atggttgcat acatgttgga gagaactg       660 gtccgcaaaa cgagattcct cccagtggct ggtggaacaa gcagtgtgta cattgaagtg      720
```

| | |
|---|---|
| ttgcatttga ctcaaggaac atgctgggaa cagatgtata ctccaggagg ggaagtgagg | 780 |
| aatgatgatg ttgatcaaag cttgattatt gctgctagga acatagtgag aagagctgca | 840 |
| gtatcagcag atccactagc atctttattg gagatgtgcc acagcacaca gattggtgga | 900 |
| attaggatgg tagacatcct taggcagaac ccaacagaag agcaagccgt ggatatatgc | 960 |
| aaggctgcaa tgggactgag aattagctca tccttcagtt ttggtggatt cacatttaag | 1020 |
| agaacaagcg gatcatcagt caagagagag aagaggtgc ttacgggcaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtca gaggtgatct gaatttcgtc aatagggcga atcaacgatt gaatcctatg | 1320 |
| catcaacttt taagacattt tcagaaggat gcgaaagtgc tttttcaaaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaatgggtg tagatgagta ctccagcacg | 1500 |
| gagagggtag tggtgagcat tgaccgtttt ttgagaatcc gggaccaacg aggaaatgta | 1560 |
| ctactgtctc ccgaggaggt cagtgaaaca cagggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtaagaac tctgttccaa caaatgaggg atgtgcttgg acatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaaggggc | 1980 |
| aattctcctg tattcaacta taacaaggcc acgaagagac tcacagttct cggaaaggat | 2040 |
| gctggcactt taactgaaga cccagatgaa ggcacagctg gagtggagtc cgctgttctg | 2100 |
| aggggattcc tcattctggg caaagaagac aagagatatg gccagcact aagcatcaat | 2160 |
| gaactgagca accttgcgaa aggagagaag gctaatgtgc taattgggca ggagacgtg | 2220 |
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 4
<211> LENGTH: 1565
<212> TYPE: DNA
<213> ORGANISM: Influenza A

<400> SEQUENCE: 4

| | |
|---|---|
| agcaaaagca gggtagataa tcactcactg agtgacatca aaatcatggc gtctcaaggc | 60 |
| accaaacgat cttacgaaca gatggagact gatggagaac gccagaatgc cactgaaatc | 120 |
| agagcatccg tcggaaaaat gattggtgga attggacgat tctacatcca atgtgcacc | 180 |
| gaactcaaac tcagtgatta tgaggggacg ttgatccaaa acagcttaac aatagagaga | 240 |
| atggtgctct ctgcttttga cgaaaggaga aataaatacc ttgaagaaca tcccagtgcg | 300 |
| gggaaagatc ctaagaaaac tggaggacct atatacagga gagtaaacgg aaagtggatg | 360 |
| agagaactca tcctttatga caaagaagaa ataaggcgca tctggcgcca agctaataat | 420 |
| ggtgacgatg caacggctgg tctgactcac atgatgatct ggcattccaa tttgaatgat | 480 |

```
gcaacttatc agaggacaag agctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcaga atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcactttc  tagcacggtc tgcactcata    840
ttgagagggt cggttgctca caagtcctgc ctgcctgcct gtgtgtatgg acctgccgta    900
gccagtgggt acgactttga aagggaggga tactctctag tcggaataga ccctttcaga    960
ctgcttcaaa acagccaagt gtacagccta atcagaccaa atgagaatcc agcacacaag   1020
agtcaactgg tgtggatggc atgccattct gccgcatttg aagatctaag agtattaagc   1080
ttcatcaaag ggacgaaggt gctcccaaga gggaagcttt ccactagagg agttcaaatt   1140
gcttccaatg aaaatatgga gactatgaa  tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccatt   1320
atggcagcat tcaatgggaa tacagagggg agaacatctg acatgaggac cgaaatcata   1380
aggatgatgg aaagtgcaag accagaagat gtgtctttcc aggggcgggg agtcttcgag   1440
ctctcggacg aaaaggcagc gagcccgatc gtgccttcct ttgacatgag taatgaagga   1500
tcttatttct tcggagacaa tgcagaggag tacgacaatt aaagaaaaat accttgtttc   1560
tact                                                                1565

<210> SEQ ID NO 5
<211> LENGTH: 1027
<212> TYPE: DNA
<213> ORGANISM: Influenza A

<400> SEQUENCE: 5
agcaaaagca ggtagatatt gaaagatgag tcttctaacc gaggtcgaaa cgtacgtact    60
ctctatcatc ccgtcaggcc ccctcaaagc cgagatcgca cagagacttg aagatgtctt   120
tgcagggaag aacaccgatc ttgaggttct catggaatgg ctaaagacaa gaccaatcct   180
gtcacctctg actaagggga ttttaggatt tgtgttcacg ctcaccgtgc ccagtgagcg   240
aggactgcag cgtagacgct ttgtccaaaa tgcccttaat gggaacgggg atccaaataa   300
catggacaaa gcagttaaac tgtataggaa gctcaagagg gagataacat tccatgggc   360 caaagaaatc tcactcagtt attctgctgg tgcacttgcc agttgtatgg cctcatata   420 caacaggatg gggctgtga ccactgaagt ggcatttggc ctggtatgtg caacctgtga   480
acagattgct gactcccagc atcggtctca taggcaaatg gtgacaacaa ccaatccact   540
aatcagacat gagaacagaa tggttttagc cagcactaca gctaaggcta tggagcaaat   600
ggctggatcg agtgagcaag cagcagaggc catggaggtt gctagtcagg ctagacaaat   660
ggtgcaagcg atgagaacca ttgggactca tcctagctcc agtgctggtc tgaaaaatga   720
tcttcttgaa aatttgcagg cctatcagaa acgaatgggg gtgcagatgc aacggttcaa   780
gtgatcctct cactattgcc gcaaatatca ttgggatctt gcacttgaca ttgtggattc   840
ttgatcgtct ttttttcaaa tgcatttacc gtcgctttaa atacgactg  aaaggagggc   900 cttctacgga aggagtgcca aagtctatga gggaagaata tcgaaaggaa cagcagagtg   960
```

-continued ctgtggatgc tgacgatggt cattttgtca gcatagagct ggagtaaaaa actaccttgt 1020
ttctact 1027

<210> SEQ ID NO 6
<211> LENGTH: 890
<212> TYPE: DNA
<213> ORGANISM: Influenza A

<400> SEQUENCE: 6
agcaaaagca gggtgacaaa aacataatgg atccaaacac tgtgtcaagc tttcaggtag 60
attgctttct ttggcatgtc cgcaaacgag ttgcagacca agaactaggc gatgccccat 120
tccttgatcg gcttcgccga gatcagaaat ccctaagagg aaggggcagt actctcggtc 180
tggacatcaa gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaga atggaccagg cgatcatgga taagaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga agataacaga gaatagtttt 780
gagcaaataa catttatgca agccttacat ctattgcttg aagtggagca agagataaga 840
actttctcgt ttcagcttat ttagtactaa aaaacaccct tgtttctact 890

<210> SEQ ID NO 7
<211> LENGTH: 1775
<212> TYPE: DNA
<213> ORGANISM: Influenza A

<400> SEQUENCE: 7
agcaaaagca ggggaaaata aaaacaacca aaatgaaggc aaacctactg gtcctgttat 60
gtgcacttgc agctgcagat gcagacacaa tatgtatagg ctaccatgcg aacaattcaa 120
ccgacactgt tgacacagta ctcgagaaga atgtgacagt gacacactct gttaacctgc 180
tcgaagacag ccacaacgga aaactatgta gattaaaagg aatagcccca ctacaattgg 240
ggaaatgtaa catcgccgga tggctcttgg gaaacccaga atgcgaccca ctgcttccag 300
tgagatcatg gtcctacatt gtagaaacac caaactctga gaatggaata tgttatccag 360
gagatttcat cgactatgag gagctgaggg agcaattgag ctcagtgtca tcattcgaaa 420
gattcgaaat atttcccaaa gaaagctcat ggcccaacca caacacaaac ggagtaacgg 480
cagcatgctc ccatgagggg aaaagcagtt tttacagaaa tttgctatgg ctgacggaga 540
aggagggctc atacccaaag ctgaaaaatt cttatgtgaa caaaaaaggg aaagaagtcc 600
ttgtactgtg ggtattcat cacccgccta acagtaagga acaacagaat ctctatcaga 660
atgaaaatgc ttatgtctct gtagtgactt caaattataa caggagattt accccggaaa 720
tagcagaaag acccaaagta agagatcaag ctgggaggat gaactattac tggaccttgc 780
taaaacccgg agacacaata atatttgagg caaatggaaa tctaatagca ccaatgtatg 840
ctttcgcact gagtagaggc tttgggtccg gcatcatcac ctcaaacgca tcaatgcatg 900

```
agtgtaacac gaagtgtcaa acacccctgg gagctataaa cagcagtctc ccttaccaga      960
atatacaccc agtcacaata ggagagtgcc caaaatacgt caggagtgcc aaattgagga     1020
tggttacagg actaaggaac attccgtcca ttcaatccag aggtctattt ggagccattg     1080
ccggttttat tgaaggggga tggactggaa tgatagatgg atggtatggt tatcatcatc     1140
agaatgaaca gggatcaggc tatgcagcgg atcaaaaaag cacacaaaat gccattaacg     1200
ggattacaaa caaggtgaac actgttatcg agaaaatgaa cattcaattc acagctgtgg     1260
gtaaagaatt caacaaatta gaaaaaagga tggaaaattt aaataaaaaa gttgatgatg     1320
gatttctgga catttggaca tataatgcag aattgttagt tctactggaa aatgaaagga     1380
ctctggattt ccatgactca aatgtgaaga atctgtatga aaagtaaaaa agccaattaa     1440
agaataatgc caaagaaatc ggaaatggat gttttgagtt ctaccacaag tgtgacaatg     1500
aatgcatgga aagtgtaaga aatgggactt atgattatcc caaatattca gaagagtcaa     1560
agttgaacag gaaaaggta gatggagtga aattggaatc aatggggatc tatcagattc     1620
tggcgatcta ctcaactgtc gccagttcac tggtgctttt ggtctccctg ggggcaatca     1680
gtttctggat gtgttctaat ggatctttgc agtgcagaat atgcatctga gattagaatt     1740
tcagagatat gaggaaaaac acccttgttt ctact                                1775

<210> SEQ ID NO 8
<211> LENGTH: 1413
<212> TYPE: DNA
<213> ORGANISM: Influenza A

<400> SEQUENCE: 8
agcaaaagca ggggtttaaa atgaatccaa atcagaaaat aataaccatt ggatcaatct      60
gtctggtagt cggactaatt agcctaatat tgcaaatagg gaatataatc tcaatatgga     120
ttagccattc aattcaaact ggaagtcaaa accatactgg aatatgcaac caaacatca     180 ttacctataa aaatagcacc tgggtaaagg acacaacttc agtgatatta accggcaatt     240
catctctttg tcccatccgt gggtgggcta tatacagcaa agacaatagc ataagaattg     300
gttccaaagg agacgttttt gtcataagag agccctttat ttcatgttct cacttggaat     360
gcaggacctt ttttctgacc caaggtgcct tactgaatga caagcattca gtgggactg     420 ttaaggacag aagcccttat agggccttaa tgagctgccc tgtcggtgaa gctccgtccc     480
cgtacaattc aagatttgaa tcggttgctt ggtcagcaag tgcatgtcat gatggcatgg     540
gctggctaac aatcggaatt tcaggtccag ataatggagc agtggctgta ttaaaataca     600
acggcataat aactgaaacc ataaaaagtt ggaggaagaa atattgagg acacaagagt     660 ctgaatgtgc ctgtgtaaat ggttcatgtt ttactatat gactgatggc ccgagtgatg     720
ggctggcctc gtacaaaatt ttcaagatcg aaaaggggaa ggttactaaa tcaatagagt     780
tgaatgcacc taattctcac tatgaggaat gttcctgtta ccctgatacc ggcaaagtga     840
tgtgtgtgtg cagagacaat tggcatggtt cgaaccggcc atgggtgtct ttcgatcaaa     900
acctggatta tcaaatagga tacatctgca gtggggtttt cggtgacaac ccgcgtcccg     960
aagatggaac aggcagctgt ggtccagtgt atgttgatgg agcaaacgga gtaaagggat    1020
tttcatatag gtatggtaat ggtgtttgga taggaaggac caaaagtcac agttccagac    1080
atgggtttga gatgatttgg gatcctaatg gatggacaga gactgatagt aagttctctg    1140
tgaggcaaga tgttgtggca atgactgatt ggtcagggta tagcggaagt ttcgttcaac    1200
```

```
atcctgagct gacagggcta gactgtatga ggccgtgctt ctgggttgaa ttaatcaggg    1260
gacgacctaa agaaaaaaca atctggacta gtgcgagcag catttctttt tgtggcgtga    1320
atagtgatac tgtagattgg tcttggccag acggtgctga gttgccattc agcattgaca    1380
agtagtctgt tcaaaaaact ccttgtttct act                                 1413
```

<210> SEQ ID NO 9
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 9

```
cacacacggt ctccgggagc gaaagcaggc a                                   31
```

<210> SEQ ID NO 10
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 10

```
ccaggacact gaaatttctt tcac                                           24
```

<210> SEQ ID NO 11
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 11

```
cacacaggtc tcctattagt agaaacaagg cattt                               35
```

<210> SEQ ID NO 12
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 12

```
cacacaggtc tccgggagcg aaagcaggtc                                     30
```

<210> SEQ ID NO 13
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 13

```
cacacacgtc tccatcatac aatcctcttg                                     30
```

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14

```
ctcctctgat ggtggcatac                                                20
```

```
<210> SEQ ID NO 15
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 15
cacacaggtc tcctattagt agaaacaagg tcgttt                    36

<210> SEQ ID NO 16
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 16
cacacacgtc tccgggagcg aaagcaggta c                         31

<210> SEQ ID NO 17
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 17
cacacacgtc tcctattagt agaaacaagg tactt                     35

<210> SEQ ID NO 18
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 18
cacacacgtc tccgggagca aaagcagggg                           30

<210> SEQ ID NO 19
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 19
cacacacgtc tcctattagt agaaacaagg gtgtttt                   37

<210> SEQ ID NO 20
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 20
cacacacgtc tccgggagca aaagcagggt a                         31

<210> SEQ ID NO 21
<211> LENGTH: 38
<212> TYPE: DNA
<213> ORGANISM: Artificial Sequence
<220> FEATURE:
```

<223> OTHER INFORMATION: A synthetic oligonucleotide

<400> SEQUENCE: 21
cacacacgtc tcctattagt agaaacaagg gtatttt          38

<210> SEQ ID NO 22
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 22
cacacaggtc tccgggagca aaagcaggag t          31

<210> SEQ ID NO 23
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 23
cacacaggtc tggtattagt agaaacaagg agttttt          38

<210> SEQ ID NO 24
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 24
cacacacgtc tccgggagca aaagcaggta g          31

<210> SEQ ID NO 25
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 25
cacacacgtc tcctattagt agaaacaagg tagtttt          38

<210> SEQ ID NO 26
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 26
cacacacgtc tccgggagca aaagcagggt g          31

<210> SEQ ID NO 27
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 27
cacacacgtc tcctattagt agaaacaagg gtgttt          37

```
<210> SEQ ID NO 28
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 28
gggtttgtat ttgtgtgtca cc                                              22

<210> SEQ ID NO 29
<211> LENGTH: 8
<212> TYPE: PRT
<213> ORGANISM: Influenza A

<400> SEQUENCE: 29

Arg Glu Arg Arg Arg Lys Lys Arg
 1               5

<210> SEQ ID NO 30
<211> LENGTH: 4
<212> TYPE: PRT
<213> ORGANISM: Artificial Sequence
<220> FEATURE:
<223> OTHER INFORMATION: A synthetic peptide

<400> SEQUENCE: 30

Thr Glu Thr Arg
 1

<210> SEQ ID NO 31
<211> LENGTH: 4
<212> TYPE: PRT
<213> ORGANISM: Artificial Sequence
<220> FEATURE:
<223> OTHER INFORMATION: A synthetic peptide

<400> SEQUENCE: 31

Arg Glu Thr Arg
 1

<210> SEQ ID NO 32
<211> LENGTH: 20
<212> TYPE: PRT
<213> ORGANISM: Artificial Sequence
<220> FEATURE:
<223> OTHER INFORMATION: A synthetic peptide

<400> SEQUENCE: 32

Cys Asn Gln Ser Ile Ile Thr Tyr Glu Asn Asn Thr Trp Val Asn Gln
 1               5                  10                  15

Thr Tyr Val Asn
            20

<210> SEQ ID NO 33
<211> LENGTH: 2341
<212> TYPE: DNA
<213> ORGANISM: Influenza A

<400> SEQUENCE: 33
agcgaaagca ggtcaattat attcaatatg gaaagaataa agaactaag aaatctaatg      60 tcgcagtctc gcacccgcga gatactcaca aaaccaccg tggaccatat ggccataatc     120
aagaagtaca catcaggaag acaggagaag aacccagcac ttaggatgaa atggatgatg   180
gcaatgaaat atccaattac agcagacaag aggataacgg aaatgattcc tgagagaaat    240
```

```
gagcaaggac aaactttatg gagtaaaatg aatgatgccg gatcagaccg agtgatggta    300
tcacctctgg ctgtgacatg gtggaatagg aatggaccaa tgacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgaag    780
aatgatgatg ttgatcaaag cttgattatt gctgctagga acatagtgag aagagctgca    840
gtatcagcag acccactagc atctttattg gagatgtgcc acagcacaca gattggtgga    900
attaggatgg tagacatcct taagcagaac ccaacagaag agcaagccgt ggatatatgc    960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatctgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtta gaggtgatct gaatttcgtc aatagggcga atcagcgact gaatcctatg    1320
catcaacttt taagacattt tcagaaggat gcgaaagtgc ttttttcaaaa ttggggagtt    1380 gaacctatcg acaatgtgat gggaatgatt gggatattgc ccgacatgac tccaagcatc    1440
gagatgtcaa tgagaggagt gagaatcagc aaaatgggtg tagatgagta ctccagcacg    1500
gagagggtag tggtgagcat tgaccggttc ttgagagtca gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg acatttgat    1860 accgcacaga taataaaact tcttcccttc gcagccgctc caccaaagca agtagaatg    1920 cagttctcct catttactgt gaatgtgagg ggatcaggaa tgagaatact tgtaaggggc    1980
aattctcctg tattcaacta caacaaggcc acgaagagac tcacagttct cggaaaggat    2040
gctggcactt taaccgaaga cccagatgaa ggcacagctg gagtggagtc cgctgttctg    2100
aggggattcc tcattctggg caaagaagac aggagatatg gccagcatt aagcatcaat    2160 gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                   2341

<210> SEQ ID NO 34
<211> LENGTH: 2341
<212> TYPE: DNA
<213> ORGANISM: Influenza A
```

<400> SEQUENCE: 34

```
agcgaaagca ggcaaaccat ttgaatggat gtcaatccga ccttactttt cttaaaagtg      60
ccagcacaaa atgctataag cacaactttc ccttataccg gagaccctcc ttacagccat     120
gggacaggaa caggatacac catggatact gtcaacagga cacatcagta ctcagaaaag     180
ggaagatgga caacaaacac cgaaactgga gcaccgcaac tcaacccgat tgatgggcca     240
ctgccagaag acaatgaacc aagtggttat gcccaaacag attgtgtatt ggaagcaatg     300
gctttccttg aggaatccca tcctggtatt tttgaaaact cgtgtattga acgatggag      360
gttgttcagc aaacacgagt agacaagctg cacaaggcc gacagaccta tgactggact      420
ttaaatagaa accagcctgc tgcaacagca ttggccaaca caatagaagt gttcagatca     480
aatggcctca cggccaatga gtcaggaagg ctcatagact tccttaagga tgtaatggag     540
tcaatgaaaa aagaagaaat ggggatcaca actcattttc agagaaagag acgggtgaga     600
gacaatatga ctaagaaaat gataacacag agaacaatag gtaaaggaa acagagattg      660
aacaaaaggg gttatctaat tagagcattg accctgaaca caatgaccaa agatgctgag     720
agagggaagc taaaacggag agcaattgca accccaggga tgcaaataag ggggtttgta     780
tactttgttg agacactggc aaggagtata tgtgagaaac ttgaacaatc agggttgcca     840
gttggaggca atgagaagaa agcaaagttg gcaaatgttg taaggaagat gatgaccaat     900
tctcaggaca ccgaactttc tttcaccatc actggagata caccaaatg gaacgaaaat      960
cagaatcctc ggatgttttt ggccatgatc acatatatga ccagaaatca gcccgaatgg    1020
ttcagaaatg ttctaagtat tgctccaata atgttctcaa acaaaatggc gagactggga    1080
aagggtata tgtttgagag caagagtatg aaacttagaa ctcaaatacc tgcagaaatg    1140
ctagcaagca ttgatttgaa atatttcaat gattcaacaa gaagaagat tgaaaaaatc    1200
cgaccgctct aatagaggg gactgcatca ttgagccctg aatgatgat gggcatgttc      1260
aatatgttaa gcactgtatt aggcgtctcc atcctgaatc ttggacaaaa gagatacacc    1320
aagactactt actggtggga tggtcttcaa tcctctgacg atttgctct gattgtgaat    1380
gcacccaatc atgaaggat tcaagccgga gtcgacaggt tttatcgaac ctgtaagcta    1440
cttggaatca atatgagcaa gaaaaagtct tacataaaca gaacaggtac atttgaattc    1500
acaagtttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat agaggtgaca cacaaataca aacccgaaga    1740
tcatttgaaa taaagaaact gtgggagcaa acccgttcca aagctggact gctggtctcc    1800
gacggaggcc caaatttata caacattaga atctccaca ttcctgaagt ctgcctaaaa    1860
tgggaattga tggatgagga ttaccagggg cgtttatgca acccactgaa ccatttgtc     1920
agccataaag aaattgaatc aatgaacaat gcagtgatga tgccagcaca tggtccagcc    1980
aaaaacatgg agtatgatgc tgttgcaaca acacactcct ggatccccaa agaaatcga    2040
tccatcttga atacaagtca aagaggagta cttgaagatg aacaaatgta ccaaaggtgc    2100
tgcaatttat ttgaaaaatt cttccccagc agttcataca agaaccagt cgggatatcc    2160
agtatggtgg aggctatggt ttccagagcc cgaattgatg cacggattga tttcgaatct    2220
ggaaggataa gaagaagaga gttcactgag atcatgaaga tctgttccac cattgaagag    2280
ctcagacggc aaaaatagtg aatttagctt gtccttcatg aaaaaatgcc ttgtttctac    2340
``` t                                                                    2341

<210> SEQ ID NO 35
<211> LENGTH: 2233
<212> TYPE: DNA
<213> ORGANISM: Influenza A

<400> SEQUENCE: 35
agcgaaagca ggtactgatt caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agatttccac 180
ttcatcaatg agcaaggcga gtcaataatc gtagaacttg gtgatcctaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggaaaata gattcatcga aattggagta acaaggagag aagttcacat atactatctg 420
gaaaaggcca ataaaattaa atctgagaaa acacacatcc acattttctc gttcactggg 480
gaagaaatgg ccacaagggc cgactacact ctcgatgaag aaagcagggc taggatcaaa 540
accaggctat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaaaaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagttcaac 1260
aaggcatgcg aactgacaga ttcaagctgg atagagcttg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt acttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacaca aatgggagaa gtactgtgtt cttgagatag gagatatgct tctaagaagt 1680
gccataggcc aggtttcaag gcccatgttc ttgtatgtga ggacaaatgg aacctcaaaa 1740
attaaaatga aatggggaat ggagatgagg cgttgtctcc tccagtcact tcaacaaatt 1800
gagagtatga ttgaagctga gtcctctgtc aaagagaaag acatgaccaa agagttcttt 1860
gagaacaaat cagaaacatg gcccattgga gagtctccca aaggagtgga ggaaagttcc 1920
attgggaagg tctgcaggac tttattagca aagtcggtat ttaacagctt gtatgcatct 1980
ccacaactag aaggattttc agctgaatca agaaaactgc ttcttatcgt tcaggctctt 2040

| agggacaatc tggaacctgg gacctttgat cttgggggc tatatgaagc aattgaggag | 2100 |
| tgcctaatta atgatccctg gttttgctt aatgcttctt ggttcaactc cttccttaca | 2160 |
| catgcattga gttagttgtg gcagtgctac tatttgctat ccatactgtc caaaaagta | 2220 |
| ccttgtttct act | 2233 |

<210> SEQ ID NO 36
<211> LENGTH: 1565
<212> TYPE: DNA
<213> ORGANISM: Influenza A

<400> SEQUENCE: 36

| agcaaaagca gggtagataa tcactcactg agtgacatca aaatcatggc gtcccaaggc | 60 |
| accaaacggt cttacgaaca gatggagact gatggagaac gccagaatgc cactgaaatc | 120 |
| agagcatccg tcggaaaaat gattggtgga attggacgat tctacatcca aatgtgcaca | 180 |
| gaacttaaac tcagtgatta tgagggacgg ttgatccaaa acagcttaac aatagagaga | 240 |
| atggtgctct ctgcttttga cgaaaggaga aataaatacc tggaagaaca tcccagtgcg | 300 |
| gggaaagatc ctaagaaaac tggaggacct atatacagaa gagtaaacgg aaagtggatg | 360 |
| agagaactca tcctttatga caaagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag ggctcttgtt cgcaccggaa tggatccag atgtgctct | 540 |
| ctgatgcaag gttcaactct ccctaggagg tctggagccg caggtgctgc agtcaaagga | 600 |
| gttggaacaa tggtgatgga attggtcagg atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcactttc tagcacggtc tgcactcata | 840 |
| ttgagagggt cggttgctca caagtcctgc ctgcctgcct gtgtgtatgg acctgccgta | 900 |
| gccagtgggt acgactttga agagaggga tactctctag tcggaataga cccttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattgagc | 1080 |
| ttcatcaaag gacgaaggt ggtcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccgtt | 1320 |
| atggcagcat tcactgggaa tacagagggg agaaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

<210> SEQ ID NO 37
<211> LENGTH: 1027
<212> TYPE: DNA
<213> ORGANISM: Influenza A

<400> SEQUENCE: 37

| agcaaaagca ggtagatatt gaaagatgag tcttctaacc gaggtcgaaa cgtacgttct | 60 |

```
ctctatcatc ccgtcaggcc ccctcaaagc cgagatcgca cagagacttg aagatgtctt       120
tgcagggaag aacaccgatc ttgaggttct catggaatgg ctaaagacaa gaccaatcct       180
gtcacctctg actaagggga ttttaggatt tgtgttcacg ctcaccgtgc ccagtgagcg       240
aggactgcag cgtagacgct ttgtccaaaa tgcccttaat gggaacgggg atccaaataa       300
catggacaaa gcagttaaac tgtataggaa gctcaagagg gagataacat tccatggggc       360
caaagaaatc tcactcagtt attctgctgg tgcacttgcc agttgtatgg gcctcatata       420
caacaggatg ggggctgtga ccactgaagt ggcatttggc ctggtatgtg caacctgtga       480
acagattgct gactcccagc atcggtctca taggcaaatg gtgacaacaa ccaacccact       540
aatcagacat gagaacagaa tggttttagc cagcactaca gctaaggcta tggagcaaat       600
ggctggatcg agtgagcaag cagcagaggc catggaggtt gctagtcagg ctaggcaaat       660
ggtgcaagcg atgagaacca ttgggactca tcctagctcc agtgctggtc tgaaaaatga       720
tcttcttgaa aatttgcagg cctatcagaa acgaatgggg gtgcagatgc aacggttcaa       780
gtgatcctct cgctattgcc gcaaatatca ttgggatctt gcacttgata ttgtggattc       840
ttgatcgtct ttttttcaaa tgcatttacc gtcgctttaa atacgactg aaaggagggc       900 cttctacgga aggagtgcca aagtctatga gggaagaata tcgaaggaa cagcagagtg       960 ctgtggatgc tgacgatggt cattttgtca gcatagagct ggagtaaaaa actaccttgt      1020
ttctact                                                                1027

<210> SEQ ID NO 38
<211> LENGTH: 890
<212> TYPE: DNA
<213> ORGANISM: Influenza A

<400> SEQUENCE: 38
agcaaaagca gggtgacaaa gacataatgg atccaaacac tgtgtcaagc tttcaggtag        60
attgctttct ttggcatgtc cgcaaacgag ttgcagacca agaactaggt gatgccccat       120
tccttgatcg gcttcgccga gatcagaaat ccctaagagg aaggggcagc actcttggtc       180
tggacatcga gacagccaca cgtgctggaa agcagatagt ggagcggatt ctgaaagaag       240
aatccgatga ggcacttaaa atgaccatgg cctctgtacc tgcgtcgcgt tacctaaccg       300
acatgactct tgaggaaatg tcaagggaat ggtccatgct catacccaag cagaaagtgg       360
caggccctct ttgtatcaga atggaccagg cgatcatgga taaaaacatc atactgaaag       420
cgaacttcag tgtgattttt gaccggctgg agactctaat attgctaagg ctttcaccg       480 aagagggagc aattgttggc gaaatttcac cattgccttc tcttccagga catactgctg       540
aggatgtcaa aaatgcagtt ggagtcctca tcggaggact tgaatggaat gataacacag       600
ttcgagtctc tgaaactcta cagagattcg cttggagaag cagtaatgag aatgggagac       660
ctccactcac tccaaaacag aaacgagaaa tggcgggaac aattaggtca gaagtttgaa       720
gaaataagat ggttgattga agaagtgaga cacaaactga aggtaacaga gaatagtttt       780
gagcaaataa catttatgca agccttacat ctattgcttg aagtggagca agagataaga       840
actttctcat ttcagcttat taataataaa aaacacccct tgtttctact                  890
```

HIGH TITER RECOMBINANT INFLUENZA VIRUSES FOR VACCINES

GOVERNMENT SUPPORT

This invention was made with government support under Grant Number AI044386 from the National Institutes of Health. The United States Government has certain rights in the invention.

BACKGROUND

Negative-sense RNA viruses are classified into seven families (*Rhabdoviridae, Paramyxoviridae, Filoviridae, Bornaviridae, Orthomyxoviridae, Bunyaviridae*, and *Arenaviridae*) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to MRNA and therefore is not infectious by itself. In order to initiate viral transcription and replication, the vRNA has to be transcribed into a plus-sense MRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both CRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

In order to initiate viral replication of negative-stranded RNA viruses, vRNA(s) or cRNA(s) must be coexpressed with the polymerase complex and the nucleoprotein. Rabies virus was the first non-segmented negative-sense RNA virus which was generated entirely from cloned cDNA: Schnell et al. (1994) generated recombinant rabies virus by cotransfection of a cDNA construct encoding the full-length cRNA and protein expression constructs for the L, P, and N proteins, all under control of the T7 RNA polymerase promoter. Infection with recombinant vaccinia virus, which provided T7 RNA polymerase, resulted in the generation of infectious rabies virus. In this T7 polymerase system, the primary transcription of the full length CRNA under control of the T7 RNA polymerase resulted in a non-capped cRNA transcript. However, three guanidine nucleotides, which form the optimal initiation sequence for T7 RNA polymerase, were attached to the 5' end. In order to create an authentic 3' end of the cRNA transcript which is essential for a productive infective cycle, the hepatitis delta ribozyme (HDVRz) sequence was used for exact autocatalytic cleavage at the 3' end of the cRNA transcript.

Since the initial report by Schnell et al. (1994), reverse genetics systems using similar techniques led to the generation of many non-segmented negative strand RNA viruses (Conzelmann, 1996; Conzelmann, 1998; Conzelmann et al., 1996; Marriott et al., 1999; Munoz et al., 2000; Nagai, 1999; Neumann et al., 2002; Roberts et al., 1998; Rose, 1996). Refinements of the original rescue procedure included the expression of T7 RNA polymerase from stably transfected cell lines (Radecke et al., 1996) or from protein expression plasmids (Lawson et al., 1995), or heat shock procedures to increase rescue efficiencies (Parks et al., 1999). Based on the T7 polymerase system, Bridgen and Elliott (1996) created Bunyamwera virus (family Bunyaviridae) from cloned cDNAs and demonstrated the feasibility of artificially generating a segmented negative-sense RNA virus by the T7 polymerase system.

In 1999, a plasmid-based reverse genetics technique was generated based on the cellular RNA polymerase I for the generation of segmented influenza A virus entirely from cloned cDNAs (Fodor et al., 1999; Neumann and Kawaoka, 1999). RNA polymerase I, a nucleolar enzyme, synthesizes ribosomal RNA which, like influenza virus RNA, does not contain 5' cap or 3' polyA structures. The RNA polymerase I transcription of a construct containing an influenza viral cDNA, flanked by RNA polymerase I promoter and terminator sequences, resulted in influenza vRNA synthesis (Fodor et al., 1999; Neumann and Kawaoka, 1999; Neumann and Kawaoka, 2001; Pekosz et al., 1999). The system was highly efficient, producing more than $10^8$ infectious virus particles per ml of supernatant of plasmid-transfected cells 48 hours post-transfection.

What is needed is a method to prepare high titer orthomyxoviruses such as influenza A virus, entirely from cloned cDNAs.

SUMMARY OF THE INVENTION

The invention provides a composition comprising a plurality of influenza virus vectors of the invention, e.g., those useful to prepare reassortant viruses including 7:1 reassortants, 6:1:1 reassortants, 5:1:2 reassortants, and 5:1:1:1 reassortants. In one embodiment of the invention, the composition includes vectors for vRNA production selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence. The composition also includes vectors for viral protein production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. Preferably, the vectors encoding viral proteins further comprise a transcription termination sequence.

In one embodiment, the cDNAs for PB1, PB2, PA, NP, M, and NS, and optionally NA, have sequences for PB1, PB2, PA, NP, M, and NS, and optionally NA, from an influenza virus that replicates to high titers in embryonated eggs, and the cDNA for HA has sequences from a different strain of influenza virus (from a heterologous influenza virus isolate with the same or a different HA subtype, i.e., a heterologous HA). For HA from pathogenic H5N1 viruses which do not grow to high titers in embryonated eggs, the cDNA for at least NA has sequences from a N1 influenza virus that replicates to high titers in embryonated eggs.

In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ EID$_{50}$/mL, e.g., $10^9$ EID$_{50}$/mL, $10^{10}$ EID$_{50}$/mL, or more, influenza virus. Reassortants within the scope of the invention that have high titers in embryonated eggs have titers of at least about $10^9$ EID$_{50}$/mL for 5:1:1:1 reassortants (with NS K55), 5:1:2 reassortants (with NS K55) and 6:1:1 reassortants (with NS K55) and at least $4 \times 10^8$ PFU/mL for 5:1:1:1 reassortants (with NS K55E) or 5:1:2 reassortants (with NS K55E). Reassortants within the scope of the invention that have high titers in MDCK cells have titers of at least $0.75 \times 10^8$ PFU/mL, e.g., at least $2.0 \times 10^8$ PFU/mL, for 5:1:1:1 or 6:1:1.

In one embodiment, the invention includes a composition comprising a plurality of influenza virus vectors for a 5:1:2 or a 6:1:1 reassortant. The composition includes a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence. The cDNAs for PB1, PB2, PA, NP, and M have sequences that are from one or more influenza viruses that replicate to high titers in embryonated eggs, wherein the cDNA for NS is from the one or more influenza viruses that replicate to high titers in embryonated eggs, and the cDNA for NA is from the one or more influenza viruses that replicate to high titers in embryonated eggs or has sequences for a heterologous NA. The cDNA for HA has sequences for a heterologous HA, which is heterologous to at least the viral gene segments for PB1, PB2, PA, NP, and M. In one embodiment, the cDNA for NS has a Glu at position 55. The composition also includes a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2. In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ EID$_{50}$/mL, e.g., $10^9$ EID$_{50}$/mL, $10^{10}$ EID$_{50}$/mL, or more, influenza virus.

In one embodiment, a composition comprising a plurality of influenza virus vectors for a 5:1:1:1 or 6:1:1 reassortant. The composition includes comprising a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence. The cDNAs for PB1, PB2, PA, NP, and M have sequences from one or more influenza viruses that replicate to high titers in MDCK cells, wherein the cDNA for NS is from the one or more influenza viruses that replicate to high titers in MDCK cells, wherein the cDNA for NA may have sequences for a heterologous NA, and wherein the cDNA for HA has sequences for a heterologous HA. The composition also includes a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2. In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ EID$_{50}$/mL, e.g., $10^9$ EID$_{50}$/mL, $10^{10}$ EID$_{50}$/mL, or more, influenza virus.

As described herein, recombinant (6:2 reassortant) viruses grow less well in eggs than does the wild-type PR8 strain, even though they possess the same PR8 "internal" genes (i.e., those other than the HA and NA). Since vigorous growth in eggs is an essential property of vaccine seed viruses used in the production of inactivated vaccines, H5N1 vaccine candidates were generated that grow as well as the PR8 donor strain in eggs. It was found that HA-NA balance and PB1 function are important growth determinants. With this knowledge, a series of H5N1 viruses was produced with altered HA-NA combinations, with the PR8 background, to assess their growth in eggs against more conventional 6:2 reassortants, including the WHO-recommended NIBRG-14 virus. A 7:1 reassortant virus and one of the 6:2 reassortants showed enhanced growth in eggs. Thus, for vaccine viruses that generally produce low titers in eggs, replacement of at least the NA of the vaccine virus with the NA of an influenza virus that grows well in eggs, or replacement of all but the HA and NA, or all but the HA, of the vaccine virus, with the other viral gene segments from an influenza virus that grows to high titers in eggs, can result in significantly higher viral titers. The titers of the reassortant viruses of the invention may be 2-fold, 3-fold, or greater, e.g., 7-fold or greater, than the corresponding nonreassortant vaccine virus. As also described herein, the internal genes responsible for the high growth rate of reassortants in eggs having genes from two different PR8 virus isolates was determined. The highest viral titers were those where the majority of internal genes were from PR8HG (PR8(UW)). In particular, 5:1:2 reassortants (PR8(UW) PB1, PB2, PA, NP and M; PR8(Cam) NS; and H5N1 HA and NA) and 6:1:1 reassortants (PR8(UW) NA, PB1, PB2, PA, NP and M; PR8(Cam) NS; and H5 HA) had high titers in eggs.

As also described herein, the viral genes responsible for a high growth rate in MDCK cells, cells likely to be approved as a source of vaccine virus, was assessed. The highest growth rate in MDCK cells was found with PB2 from PR8(UW), NS from PR8(Cam) or NS K55E from PR8(UW), and a NA with a long stalk, e.g., a stalk greater than 20 mino acids but less than about 100 amino acids, e.g., greater than about 40 and up to about 80 amino acids in lemgth. Thus 5:1:1:1 and 6:1:1 reassortants with PR8(UW) PA, PB1, PB2, NP and M, and NS K55E from PR8(UW) or PR8(Cam), NA from PR8(UW) or a heterologous NA source, and a heterologous HA, grew to the highest titers in MDCK cells.

In one embodiment, the nucleic acid molecule corresponds to a sequence encoding PB1, PB2, PA, NP, M, and NS, and optionally NA, having substantially the same activity as a corresponding polypeptide encoded by one of SEQ ID NOs: 1-6 or 8. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid molecule corresponds to a sequence encoding a polypeptide which is substantially the same as, e.g., having at least 80%, e.g., 90%, 92%, 95%, 97% or 99%, contiguous amino acid sequence identity to, a polypeptide encoded by one of SEQ ID NOs: 1-6 or 8. In one embodiment, the isolated and/or purified nucleic acid molecule comprises a nucleotide sequence which is substantially the same as, e.g., having at least 50%, e.g., 60%, 70%, 80% or 90% or more contiguous nucleic acid sequence identity to, one of SEQ ID NOs: 1-6, 8, or 33 to 38 and, in one embodiment, also encodes a polypeptide having at least 80%, e.g., 90%, 92%, 95%, 97% or 99%, contiguous amino acid sequence identity to a polypeptide encoded by one of SEQ ID NOs: 1-6, 8, or 33 to 38. In one embodiment, the isolated and/or purified nucleic acid molecule encodes a polypeptide with one or more, for instance, 2, 5, 10, 15, 20 or more, conservative amino acids substitutions, e.g., conservative substitutions of up to 10% or 20% of the residues, relative to a polypeptide encoded by one of SEQ ID NOs: 1-6 or 8. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the isolated and/or purified nucleic acid molecule encodes a polypeptide with one or more, for instance, 2, 3 or 4, nonconservative amino acid substitutions, relative to a polypeptide encoded by one of SEQ ID NOs:1-6 or 33-38. For instance, a K55E NS and a S360Y PB2 substitution are nonconservative substitutions.

In another embodiment, the nucleic acid molecule having PB1, PB2, PA, NP, M, and NS, and optionally NA, sequences, or the complement thereof, hybridizes to one of SEQ ID NOs: 1-6, 8, or 33 to 38, the complement thereof, under low stringency, moderate stringency or stringent conditions. For example, the following conditions may be employed: 7% sodium dodecyl sulfate (SDS), 0.5 M NaPO$_4$, 1 mM EDTA at 50° C. with washing in 2X SSC, 0.1% SDS at 50° C. (low stringency), more desirably in 7% sodium dodecyl sulfate (SDS), 0.5 M NaPO$_4$, 1 mM EDTA at 50° C. with washing in 1X SSC, 0.1% SDS at 50° C. (moderate stringency), more desirably still in 7% sodium dodecyl sulfate (SDS), 0.5 M NaPO$_4$, 1 mM EDTA at 50° C. with washing in 0.5X SSC, 0.1% SDS at 50° C. (stringent), preferably in 7% sodium dodecyl sulfate (SDS), 0.5 M NaPO$_4$, 1 mM EDTA at 50° C. with washing in 0.1X SSC, 0.1% SDS at 50° C. (more stringent), more preferably in 7% sodium dodecyl sulfate (SDS), 0.5 M NaPO$_4$, 1 mM EDTA at 50° C. with washing in 0.1X SSC, 0.1% SDS at 65° C. (very stringent). In one embodiment, the nucleic acid molecule encodes a polypeptide which is substantially the same as, e.g., having at least 50%, e.g., 60%, 70%, 80% or 90% or more contiguous nucleic acid sequence identity to, one of SEQ ID NOs: 1-6, or 33 to 38, and preferably has substantially the same activity as a corresponding full-length polypeptide encoded by one of SEQ ID NOs: 1-6, 8 or 33 to 28. Those nucleic acid molecules, or nucleic acid molecules from other Ni strains that grow well in eggs, may be employed with nucleic acid for any HA, e.g., H5.

Thus, nucleic acid molecule may be employed to express influenza proteins, to prepare chimeric genes, e.g., with other viral genes including other influenza virus genes, and/or to prepare recombinant virus. Thus, the invention also provides isolated polypeptides, recombinant virus, and host cells contacted with the nucleic acid molecules or recombinant virus of the invention.

The invention also provides a plurality of the following isolated and/or purified vectors: a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, a vector comprising a promoter operably linked to an influenza virus NS cDNA linked to a transcription termination sequence, wherein at least one vector comprises sequences corresponding to those encoding PB1, PB2, PA, NP, M, NS, and optionally NA, or a portion thereof, having substantially the same activity as a corresponding polypeptide encoded by one of SEQ ID NOs: 1-6 or 8, e.g., a sequence encoding a polypeptide with at least 80% amino acid identity to a polypeptide encoded by one of SEQ ID NOs: 1-6, 8 or 33 to 38. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

The invention includes the use of isolated and purified vectors or plasmids, which express or encode influenza virus proteins, or express or encode influenza vRNA, both native and recombinant vRNA. Preferably, the vectors comprise influenza cDNA, e.g., influenza A (e.g., any influenza A gene including any of the 15 HA or 9 NA subtypes), B or C DNA (see Chapters 45 and 46 of Fields *Virology* (Fields et al. (eds.), Lippincott-Raven Publ., Philadelphia, Pa. (1996), which are specifically incorporated by reference herein), although it is envisioned that the gene(s) of any organism may be employed in the vectors or methods of the invention. The cDNA may be in the sense or antisense orientation relative to the promoter. Thus, a vector of the invention may encode an influenza virus protein (sense) or vRNA (antisense). Any suitable promoter or transcription termination sequence may be employed to express a protein or peptide, e.g., a viral protein or peptide, a protein or peptide of a nonviral pathogen, or a therapeutic protein or peptide.

A composition of the invention may also comprise a gene or open reading frame of interest, e.g., a foreign gene encoding an immunogenic peptide or protein useful as a vaccine. Thus, another embodiment of the invention comprises a composition of the invention as described above in which one of the vectors is replaced with, or the composition further comprises, a vector comprising a promoter linked to 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof, linked to a transcription termination sequence. Preferably, the desired nucleic acid sequence such as a cDNA is in an antisense orientation. The introduction of such a composition to a host cell permissive for influenza virus replication results in recombinant virus comprising vRNA corresponding to sequences of the vector. The promoter in such a vector for vRNA production may be a RNA polymerase I promoter, a RNA polymerase II promoter, a RNA polymerase III promoter, a T7 promoter, and a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. In one embodiment, the vector comprising the desired nucleic acid sequence comprises a cDNA of interest. The cDNA of interest, whether in a vector for vRNA or protein production, may encode an immunogenic epitope, such as an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes.

A plurality of the vectors of the invention may be physically linked or each vector may be present on an individual plasmid or other, e.g., linear, nucleic acid delivery vehicle.

The promoter or transcription termination sequence in a vRNA or virus protein expression vector may be the same or different relative to the promoter or any other vector. Preferably, the vector or plasmid which expresses influenza vRNA comprises a promoter suitable for expression in at least one particular host cell, e.g., avian or mammalian host cells such as canine, feline, equine, bovine, ovine, or primate cells including human cells, or preferably, for expression in more than one host.

In one embodiment, one or more vectors for vRNA production comprise a promoter including, but not limited to, a RNA polymerase I promoter, e.g., a human RNA polymerase I promoter, a RNA polymerase II promoter, a RNA polymerase III promoter, a T7 promoter, or a T3 promoter. Preferred transcription termination sequences for the vRNA vectors include, but are not limited to, a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2 and preferably more, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

The invention also provides a method to prepare influenza virus. The method comprises contacting a cell with a plurality of the vectors of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or virus of the invention. In another embodiment, the invention includes contacting the cell with one or more vectors, either vRNA or protein production vectors, prior to other vectors, either vRNA or protein production vectors.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) is provided.

The invention also provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor-specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. Preferably, the mammal is a human.

BRIEF DESCRIPTION OF THE DRAWINGS

FIG. 1. Titer of various influenza viruses.

FIG. 2. Schematic diagram of the Ni NAs used to generate H5N1/PR8 reassortant viruses by reverse genetics. VN1203fill contains a 20 amino acid (aa) insertion derived from the N1 of the H5N1 precursor strain, GsGd96. VN1203fill.N2 contains, in addition to 20 aa from GsGd96 NA, a 14-aa insertion from N2 NA, resulting in a 34-aa insertion into the stalk of VN1203 NA. VN1202fill.N2N9 contains, in addition to 20 aa from GsGd96 NA and 14 aa from N2 NA, a 14-aa insertion from N9 NA, resulting in a 48-aa insertion into the stalk of VN1203. The predicted total length of the stalk region of each NA is given beneath each molecule.

FIG. 6. Growth comparison of H5N1/PR8 reassortant viruses in chicken embryonated eggs. Viral titers of the 6:2 and 7:1 reassortant viruses, including the WHO-recommended NIBRG-14 strain (a VN1194/PR8 6:2 reassortant virus) were compared by plaque titration with MDCK cells. Mean titers and standard deviations of 3 eggs inoculated with each virus are shown. Thus, replacing just the NA of H5N1 viruses with the NA of PR8 may improve titers in eggs.

FIG. 7. Growth of reassortant H5N1 viruses possessing PR8(UW) or PR8(Cambridge) internal genes in chicken embryonated eggs. Asterisks indicate a significant (p<0.05, Student t-test) reduction in infectivity compared to PR8 (UW)/1194.

FIG. 8. The effect of the M and NS genes on the growth of viruses in chicken embryonated eggs. The asterisk indicates a significant (p<0.05, Student t-test) increase in infectivity compared to PR8(UW)/1194.

FIG. 10. Identification of a gene segment responsible for the enhanced growth of PR8(UW)/1194 relative to NIBRG-14 in MDCK cells.

FIG. 11. Identification of the amino acid in PB2 responsible for the high growth rate of the vaccine seed virus in MDCK cells.

FIG. 12. Growth rates in MDCK cells of reassortants with different HA, NA, and NS genes. The asterisk indicates significantly better virus growth compared to that of PR8(UW)/ 1194. Double asterisks indicate significantly better growth rates compared to viruses expressing PR8(UW) NS.

FIG. 13. Growth in MDCK cells of the H5N1 vaccine seed virus containing a heterologous NS segment.

FIG. 14. Schematic of the genotype of an H5N1 vaccine seed virus with high growth capacity in chicken embryonated eggs or MDCK cells.

FIG. 15. Nucleotide sequence for PR8(Cambridge) genes (SEQ ID NOs:33-38).

DETAILED DESCRIPTION OF THE INVENTION

Definitions

Figure 3:
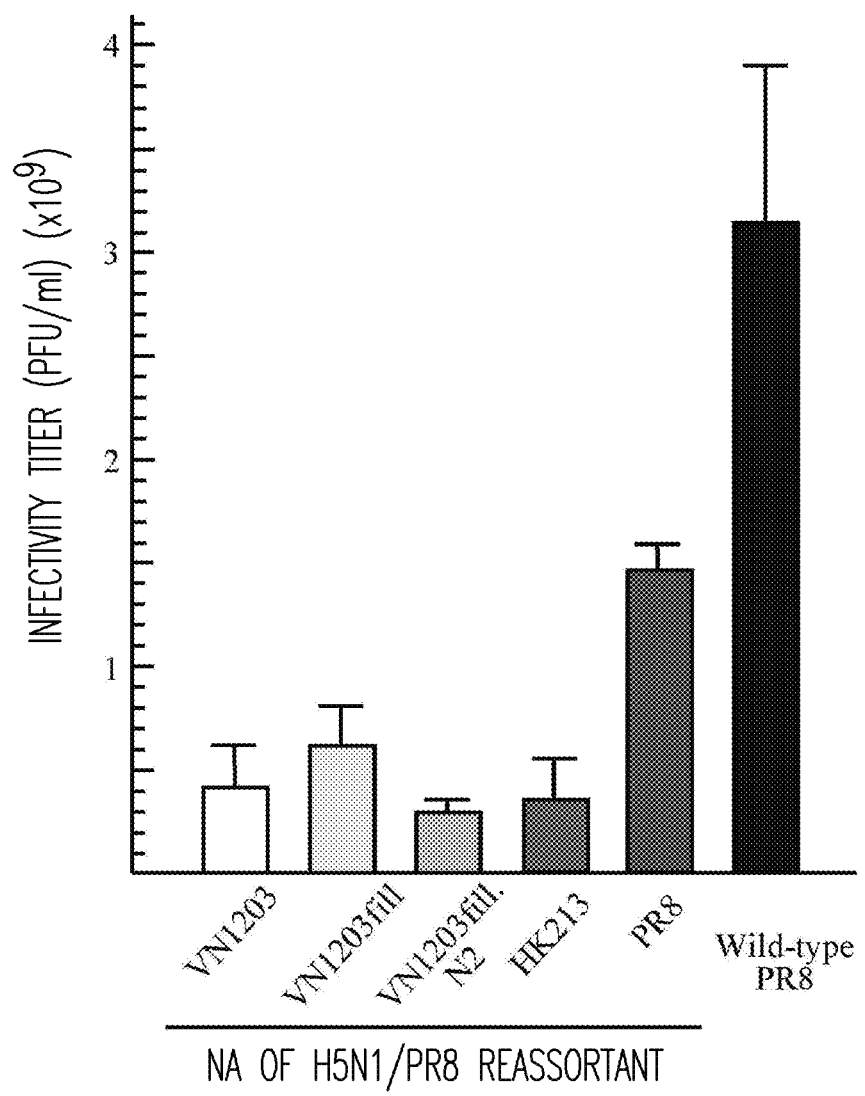
FIG. 3. Growth of H5N1/PR8 reassortant viruses in chicken embryonated eggs. The titers of the reassortant viruses containing avirulent-form VN1203 HA and either homologous NA (VN1203) or heterologous NAs (VN1203fill, VN1203fill.N2, HK213, or PR8) with a PR8 background were compared by plaque titration with MDCK cells. The titer of wild-type (egg-adapted) PR8 also is included for comparison. The data are reported as mean titers and standard deviations for 3 eggs inoculated with each virus.

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a reassortant influenza virus.

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein. Similarly, influenza C virus does not have a M2 protein.

Cell Lines and Influenza Viruses That Can Be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reasserted virus according to known methods (see, e.g., Murphy, 1993). Since resistance to influenza A virus is mediated by the development of an immune response to the HA and NA glycoproteins, the genes coding for these surface antigens must come from the reassorted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants H1N1 and H3N2 vaccine candidates in a manner analogous to that described above for the A/AA/6/60 ca donor virus. Similarly, other known and suitable attenuated donor strains can be reasserted with influenza virus of the invention to obtain attenuated vaccines suitable for use in the vaccination of mammals (Enami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; *Avery's Drug Treatment*, 1987; Osol, 1980; Katzung, 1992. The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein.

Influenza A or B virus strains having a modem antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-o, interferon-β,interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; Avery, 1987; and Katzung, 1992. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Katsung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children 3 years of age, and 7.5 μg per component for older children <3 years of age. The quantity of NA can also be standardized, however, this glycoprotein can be labile during the processor purification and storage (Kendal et al., 1980). Each 0.5-ml dose of vaccine preferably contains approximately 1-50 billion virus particles, and preferably 10 billion particles.

The invention will be further described by the following nonlimiting examples.

EXAMPLE 1

To develop a reverse genetics system for influenza A/Puerto Rico/8/34, viral RNA was extracted from the allantoic fluid of A/Puerto Rico/8/34 (H1N1), Madison high grower variant (PR8HG), using RNeasy Mini kit (Qiagen) according to the manufacturer's protocol. cDNA was synthesized using MMLV-RTase (Promega) and Uni12 primer. The cDNAs were amplified overnight by PCR using the following:

Primer Sets

```
PB1:
Ba PB1-1 and PB1-1735R (front fragment) and
PB1-903 and Ba-PB1-2341R (rear fragment)
Ba-PB1-1
                                   (SEQ ID NO:9)
CACACACGGTCTCCGGGAGCGAAAGCAGGCA 173PB1-1735R
                                  (SEQ ID NO:28)
GGGTTTGTATTTGTGTGTCACC 233PB1-903
                                  (SEQ ID NO:10)
CCAGGACACTGAAATTTCTTTCAC Ba-PB1-2341R
                                  (SEQ ID NO:11)
CACACAGGTCTCCTATTAGTAGAAACAAGGCATTT PB2:
Ba PB2-1 and B2 1260R (front fragment) and WSN PB2
seq-2 and Ba-PB2-2341R (rear fragment)
Ba-PB2-1
                                  (SEQ ID NO:12)
CACACAGGTCTCCGGGAGCGAAAGCAGGTC B2 1260R
                                  (SEQ ID NO:13)
CACACACGTCTCCATCATACAATCCTCTTG WSN PB2 seq-2
                                  (SEQ ID NO:14)
CTCCTCTGATGGTGGCATAC Ba-PB2-2341R
                                  (SEQ ID NO:15)
CACACAGGTCTCCTATTAGTAGAAACAAGGTCGTTT
```

-continued

```
PA:
Bm-PA-1
                                  (SEQ ID NO:16)
CACACACGTCTCCGGGAGCGAAAGCAGGTAC

Bm-PA-2233R
                                  (SEQ ID NO:17)
CACACACGTCTCCTATTAGTAGAAACAAGGTACTT

HA:
Bm-HA-1:
                                  (SEQ ID NO:18)
CACACACGTCTCCGGGAGCAAAAGCAGGGG

Bm-NS-890R:
                                  (SEQ ID NO:19)
CACACACGTCTCCTATTAGTAGAAACAAGGGTGTTTT

NP
Bm-NP-1
                                  (SEQ ID NO:20)
CACACACGTCTCCGGGAGCAAAAGCAGGGTA

Bm-NP-1565R
                                  (SEQ ID NO:21)
CACACACGTCTCCTATTAGTAGAAACAAGGGTATTTTT

NA:
Ba-NA-1:
                                  (SEQ ID NO:22)
CACACAGGTCTCCGGGAGCAAAAGCAGGAGT

Ba-NA-1413R:
                                  (SEQ ID NO:23)
CACACAGGTCTGGTATTAGTAGAAACAAGGAGTTTTTT

M:
Bm-M-1
                                  (SEQ ID NO:24)
CACACACGTCTCCGGGAGCAAAAGCAGGTAG

Bm-M-1027R
                                  (SEQ ID NO:25)
CACACACGTCTCCTATTAGTAGAAACAAGGTAGTTTTT

NS:
Bm-NS-1
                                  (SEQ ID NO:26)
CACACACGTCTCCGGGAGCAAAAGCAGGGTG

Bm-NS-890R
                                  (SEQ ID NO:27)
CACACACGTCTCCTATTAGTAGAAACAAGGGTGTTTT

DNA polymerase: pfu Native DNA polymerase
(Stratagene)
```

The PCR products were separated by gel electrophoresis and extracted from the agarose gel using a gel extraction kit (Qiagen). The extracted genes were ligated into pT7Blue blunt vector (Novagen) using a Takara ligation kit ver. II (Takara). After 5 hours, the ligated genes were transformed into JM109 (PB2, M, and NS genes) or DH5alpha (PA, PB1, and NP). Six colonies for each gene were cultured in TB for 8 hours. The plasmids were extracted from the bacteria culture, and four clones per gene were sequenced.

The PA, NP, M, and NS genes in pT7Blue were excised by Bsm BI enzyme (New England Biolabs). The PB1 gene was excised by Bsa I (New England Biolabs). The excised genes were ligated overnight with pPolIR vector which contains the human RNA polymerase I promoter and the mouse RNA polymerase I terminator which had been digested with Bsm BI. The front fragment of the PB2 gene in pT7Blue was excised by Bsr GI (New England Biolabs) and Bam HI (Roche), and the rear fragment was excised by Bsr GI (New England Biolabs) and Spe I (Roche). The excised fragments were mixed and digested by Bsa I. After 6 hours, the digested genes were purified using a PCR purification kit (Qiagen) and ligated overnight between the Bsm BI sites of the pPolIR vector.

The ligated PB1, PA, NP, M, and NS-pPolIR genes were used to transform JM109 (M and NS genes) or DH5alpha (PB1, PA and NP genes) overnight. The colonies of transformed bacteria were cultured in LB overnight. The ligated PB2-pPolIR was used to transform JM109 overnight.

The plasmids were extracted from the bacterial cultures and gene inserts were confirmed by enzyme digestion. The colonies of bacteria transformed by PB2-PolIR were cultured in LB for 8 hours. The plasmids were then extracted and the gene insertion was confirmed by enzyme digestion. All pPolI constructs were sequenced to ensure that they did not contain unwanted mutations.

The pPolIR constructs for PR8HG were transfected into 293T human embryonic kidney cells with A/WSN/33(WSN)-HA and NA, A/Hong Kong/483/97(HK)-HAavir and NA, or A/Kawasaki/01(Kawasaki)-HA and NA PolI constructs and four protein-expression constructs for the polymerase proteins and NP of A/WSN/33. The supernatants from transfected 293T cells were serially diluted (undiluted to $10^{-7}$) and infected into the allantoic cavities of 9-day-old embryonated chicken eggs. The allantoic fluids of the infected eggs were harvested and their virus titers tested by HA assay (Table 1).

TABLE 1

| Virus possessing PR8 genes together with the following HA and NA genes | HA titer (HAU/ml) of allantoic fluid from eggs inoculated with 293T supernatants diluted at: | | | | | | | |
|---|---|---|---|---|---|---|---|---|
| | un-diluted | $10^{-1}$ | $10^{-2}$ | $10^{-3}$ | $10^{-4}$ | $10^{-5}$ | $10^{-6}$ | $10^{-7}$ |
| WSN-HA NA | <1 | <1 | 200 | <1 | <1 | <1 | <1 | <1 |
| HK-HAavir NA | 100 | <1 | <1 | <1 | <1 | <1 | <1 | <1 |
| Kawasaki-HA NA | <1 | <1 | <1 | <1 | <1 | <1 | <1 | <1 |

HA-positive samples (virus with WSN-HA NA at $10^{-2}$ and virus with HK-HAavir NA at undiluted) were diluted serially from $10^{-2}$ to $10^{-8}$ and 100 ul of each dilution was infected into embryonated chicken eggs. The allantoic fluids of the infected eggs were harvested and their virus titers tested by HA assay (Table 2). The 50% egg infectious dose (EID$_{50}$) of A/Puerto Rico/8/34 (H1N1) prepared from plasmids was $10^{10.33}$/ml, and the HA titer was 1:3200.

A recombinant virus having the HA and NA genes from A/Hong Kong/213/2003 (H5N1) and the remainder of the type A influenza virus genes from PR8HG was prepared. The titer of the recombinant virus was $10^{10.67}$ EID$_{50}$/ml, and the HA titer was 1:1600

TABLE 2

| Virus possessing PR8 genes together with the following HA and NA genes | HA titer (HAU/ml) in each dilition | | | | | | |
|---|---|---|---|---|---|---|---|
| | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

Sequences of PR8 genes:

PA
(SEQ ID NO:1)
AGCGAAAGCA GGTACTGATC CAAAATGGAA GATTTTGTGC

GACAATGCTT

CAATCCGATG ATTGTCGAGC TTGCGGAAAA AACAATGAAA

GAGTATGGGG

AGGACCTGAA AATCGAAACA AACAAATTTG CAGCAATATG

CACTCACTTG

GAAGTATGCT TCATGTATTC AGATTTTCAC TTCATCAATG

AGCAAGGCGA

GTCAATAATC GTAGAACTTG GTGATCCAAA TGCACTTTTG

AAGCACAGAT

TTGAAATAAT CGAGGGAAGA GATCGCACAA TGGCCTGGAC

AGTAGTAAAC

AGTATTTGCA ACACTACAGG GGCTGAGAAA CCAAAGTTTC

TACCAGATTT

GTATGATTAC AAGGAGAATA GATTCATCGA AATTGGAGTA

ACAAGGAGAG

AAGTTCACAT ATACTATCTG GAAAAGGCCA ATAAAATTAA

ATCTGAGAAA

ACACACATCC ACATTTTCTC GTTCACTGGG GAAGAAATGG

CCACAAAGGC

AGACTACACT CTCGATGAAG AAAGCAGGGC TAGGATCAAA

ACCAGACTAT

TCACCATAAG ACAAGAAATG GCCAGCAGAG GCCTCTGGGA

TTCCTTTCGT

CAGTCCGAGA GAGGAGAAGA GACAATTGAA GAAAGGTTTG

AAATCACAGG

AACAATGCGC AAGCTTGCCG ACCAAAGTCT CCCGCCGAAC

TTCTCCAGCC

TTGAAAATTT TAGAGCCTAT GTGGATGGAT TCGAACCGAA

CGGCTACATT

GAGGGCAAGC TGTCTCAAAT GTCCAAAGAA GTAAATGCTA

GAATTGAACC

TTTTTTGAAA ACAACACCAC GACCACTTAG ACTTCCGAAT

GGGCCTCCCT

GTTCTCAGCG GTCCAAATTC CTGCTGATGG ATGCCTTAAA

ATTAAGCATT

GAGGACCCAA GTCATGAAGG AGAGGGAATA CCGCTATATG

ATGCAATCAA

```
ATGCATGAGA ACATTCTTTG GATGGAAGGA ACCCAATGTT
GTTAAACCAC
ACGAAAAGGG AATAAATCCA AATTATCTTC TGTCATGGAA
GCAAGTACTG
GCAGAACTGC AGGACATTGA GAATGAGGAG AAAATTCCAA
AGACTAAAAA
TATGAAGAAA ACAAGTCAGC TAAAGTGGGC ACTTGGTGAG
AACATGGCAC
CAGAAAAGGT AGACTTTGAC GACTGTAAAG ATGTAGGTGA
TTTGAAGCAA
TATGATAGTG ATGAACCAGA ATTGAGGTCG CTTGCAAGTT
GGATTCAGAA
TGAGTTTAAC AAGGCATGCG AACTGACAGA TTCAAGCTGG
ATAGAGCTCG
ATGAGATTGG AGAAGATGTG GCTCCAATTG AACACATTGC
AAGCATGAGA
AGGAATTATT TCACATCAGA GGTGTCTCAC TGCAGAGCCA
CAGAATACAT
AATGAAGGGA GTGTACATCA ATACTGCCTT GCTTAATGCA
TCTTGTGCAG
CAATGGATGA TTTCCAATTA ATTCCAATGA TAAGCAAGTG
TAGAACTAAG
GAGGGAAGGC GAAAGACCAA CTTGTATGGT TTCATCATAA
AAGGAAGATC
CCACTTAAGG AATGACACCG ACGTGGTAAA CTTTGTGAGC
ATGGAGTTTT
CTCTCACTGA CCCAAGACTT GAACCACATA AATGGGAGAA
GTACTGTGTT
CTTGAGATAG GAGATATGCT TATAAGAAGT GCCATAGGCC
AGGTTTCAAG
GCCCATGTTC TTGTATGTGA GAACAAATGG AACCTCAAAA
ATTAAAATGA
AATGGGGAAT GGAGATGAGG CGTTGCCTCC TCCAGTCACT
TCAACAAATT
GAGAGTATGA TTGAAGCTGA GTCCTCTGTC AAAGAGAAAG
ACATGACCAA
AGAGTTCTTT GAGAACAAAT CAGAAACATG GCCCATTGGA
GAGTCCCCCA
AAGGAGTGGA GGAAAGTTCC ATTGGGAAGG TCTGCAGGAC
TTTATTAGCA
AAGTCGGTAT TCAACAGCTT GTATGCATCT CCACAACTAG
AAGGATTTTC
AGCTGAATCA AGAAAACTGC TTCTTATCGT TCAGGCTCTT
AGGGACAACC
TGGAACCTGG GACCTTTGAT CTTGGGGGGC TATATGAAGC
AATTGAGGAG
TGCCTGATTA ATGATCCCTG GGTTTTGCTT AATGCTTCTT
GGTTCAACTC
CTTCCTTACA CATGCATTGA GTTAGTTGTG GCAGTGCTAC
TATTTGCTAT
CCATACTGTC CAAAAAGTA CCTTGTTTCT ACT
PB1                                      (SEQ ID NO:2)
AGCGAAAGCA GGCAAACCAT TTGAATGGAT GTCAATCCGA
CCTTACTTTT CTTAAAAGTG CCAGCACAAA ATGCTATAAG
CACAACTTTC
CCTTATACTG GAGACCCTCC TTACAGCCAT GGGACAGGAA
CAGGATACAC
CATGGATACT GTCAACAGGA CACATCAGTA CTCAGAAAAG
GGAAGATGGA
CAACAAACAC CGAAACTGGA GCACCGCAAC TCAACCCGAT
TGATGGGCCA
CTGCCAGAAG ACAATGAACC AAGTGGTTAT GCCCAAACAG
ATTGTGTATT
GGAGGCGATG GCTTTCCTTG AGGAATCCCA TCCTGGTATT
TTTGAAAACT
CGTGTATTGA AACGATGGAG GTTGTTCAGC AAACACGAGT
AGACAAGCTG
ACACAAGGCC GACAGACCTA TGACTGGACT CTAAATAGAA
ACCAACCTGC
TGCAACAGCA TTGGCCAACA CAATAGAAGT GTTCAGATCA
AATGGCCTCA
CGGCCAATGA GTCTGGAAGG CTCATAGACT TCCTTAAGGA
TGTAATGGAG
TCAATGAACA AAGAAGAAAT GGGGATCACA ACTCATTTTC
AGAGAAAGAG
ACGGGTGAGA GACAATATGA CTAAGAAAAT GATAACACAG
AGAACAATGG
GTAAAAGAA GCAGAGATTG AACAAAAGGA GTTATCTAAT
TAGAGCATTG
ACCCTGAACA CAATGACCAA AGATGCTGAG AGAGGGAAGC
TAAAACGGAG
```

```
AGCAATTGCA ACCCCAGGGA TGCAAATAAG GGGGTTTGTA

TACTTTGTTG

AGACACTGGC AAGGAGTATA TGTGAGAAAC TTGAACAATC

AGGGTTGCCA

GTTGGAGGCA ATGAGAAGAA AGCAAAGTTG GCAAATGTTG

TAAGGAAGAT

GATGACCAAT TCTCAGGACA CCGAACTTTC TTTCACCATC

ACTGGAGATA

ACACCAAATG GAACGAAAAT CAGAATCCTC GGATGTTTTT

GGCCATGATC

ACATATATGA CCAGAAATCA GCCCGAATGG TTCAGAAATG

TTCTAAGTAT

TGCTCCAATA ATGTTCTCAA ACAAAATGGC GAGACTGGGA

AAAGGGTATA

TGTTTGAGAG CAAGAGTATG AAACTTAGAA CTCAAATACC

TGCAGAAATG

CTAGCAAGCA TCGATTTGAA ATATTTCAAT GATTCAACAA

GAAAGAAGAT

TGAAAAAATC CGACCGCTCT AATAGAGGG GACTGCATCA

TTGAGCCCTG

GAATGATGAT GGGCATGTTC AATATGTTAA GCACTGTATT

AGGCGTCTCC

ATCCTGAATC TTGGACAAAA GAGATACACC AAGACTACTT

ACTGGTGGGA

TGGTCTTCAA TCCTCTGACG ATTTTGCTCT GATTGTGAAT

GCACCCAATC

ATGAAGGGAT TCAAGCCGGA GTCGACAGGT TTTATCGAAC

CTGTAAGCTA

CTTGGAATCA ATATGAGCAA GAAAAAGTCT TACATAAACA

GAACAGGTAC

ATTTGAATTC ACAAGTTTTT TCTATCGTTA TGGGTTTGTT

GCCAATTTCA

GCATGGAGCT TCCCAGTTTT GGGGTGTCTG GGATCAACGA

GTCAGCGGAC

ATGAGTATTG GAGTTACTGT CATCAAAAAC AATATGATAA

ACAATGATCT

TGGTCCAGCA ACAGCTCAAA TGGCCCTTCA GTTGTTCATC

AAAGATTACA

GGTACACGTA CCGATGCCAT ATAGGTGACA CACAAATACA

AACCCGAAGA

TCATTTGAAA TAAAGAAACT GTGGGAGCAA ACCCGTTCCA

AAGCTGGACT

GCTGGTCTCC GACGGAGGCC CAAATTTATA CAACATTAGA

AATCTCCACA

TTCCTGAAGT CTGCCTAAAA TGGGAATTGA TGGATGAGGA

TTACCAGGGG

CGTTTATGCA ACCCACTGAA CCCATTTGTC AGCCATAAAG

AAATTGAATC

AATGAACAAT GCAGTGATGA TGCCAGCACA TGGTCCAGCC

AAAAACATGG

AGTATGATGC TGTTGCAACA ACACACTCCT GGATCCCCAA

AAGAAATCGA

TCCATCTTGA ATACAAGTCA AGAGGAGTA CTTGAGGATG

AACAAATGTA

CCAAAGGTGC TGCAATTTAT TTGAAAAATT CTTCCCCAGC

AGTTCATACA

GAAGACCAGT CGGGATATCC AGTATGGTGG AGGCTATGGT

TTCCAGAGCC

CGAATTGATG CACGGATTGA TTTCGAATCT GGAAGGATAA

AGAAAGAAGA

GTTCACTGAG ATCATGAAGA TCTGTTCCAC CATTGAAGAG

CTCAGACGGC

AAAAATAGTG AATTTAGCTT GTCCTTCATG AAAAAATGCC

TTGTTTCTAC T

PB2                                      (SEQ ID NO:3)

AGCGAAAGCA GGTCAATTAT ATTCAATATG GAAAGAATAA

AAGAACTACG

AAATCTAATG TCGCAGTCTC GCACCCGCGA GATACTCACA

AAAACCACCG

TGGACCATAT GGCCATAATC AAGAAGTACA CATCAGGAAG

ACAGGAGAAG

AACCCAGCAC TTAGGATGAA ATGGATGATG GCAATGAAAT

ATCCAATTAC

AGCAGACAAG AGGATAACGG AAATGATTCC TGAGAGAAAT

GAGCAAGGAC

AAACTTTATG GAGTAAAATG AATGATGCCG GATCAGACCG

AGTGATGGTA

TCACCTCTGG CTGTGACATG GTGGAATAGG AATGGACCAA

TAACAAATAC

AGTTCATTAT CCAAAAATCT ACAAAACTTA TTTTGAAAGA

GTCGAAAGGC
```

```
TAAAGCATGG AACCTTTGGC CCTGTCCATT TTAGAAACCA
AGTCAAAATA
CGTCGGAGAG TTGACATAAA TCCTGGTCAT GCAGATCTCA
GTGCCAAGGA
GGCACAGGAT GTAATCATGG AAGTTGTTTT CCCTAACGAA
GTGGGAGCCA
GGATACTAAC ATCGGAATCG CAACTAACGA TAACCAAAGA
GAAGAAAGAA
GAACTCCAGG ATTGCAAAAT TTCTCCTTTG ATGGTTGCAT
ACATGTTGGA
GAGAGAACTG GTCCGCAAAA CGAGATTCCT CCCAGTGGCT
GGTGGAACAA
GCAGTGTGTA CATTGAAGTG TTGCATTTGA CTCAAGGAAC
ATGCTGGGAA
CAGATGTATA CTCCAGGAGG GGAAGTGAGG AATGATGATG
TTGATCAAAG
CTTGATTATT GCTGCTAGGA ACATAGTGAG AAGAGCTGCA
GTATCAGCAG
ATCCACTAGC ATCTTTATTG GAGATGTGCC ACAGCACACA
GATTGGTGGA
ATTAGGATGG TAGACATCCT TAGGCAGAAC CCAACAGAAG
AGCAAGCCGT
GGATATATGC AAGGCTGCAA TGGGACTGAG AATTAGCTCA
TCCTTCAGTT
TTGGTGGATT CACATTTAAG AGAACAAGCG GATCATCAGT
CAAGAGAGAG
GAAGAGGTGC TTACGGGCAA TCTTCAAACA TTGAAGATAA
GAGTGCATGA
GGGATATGAA GAGTTCACAA TGGTTGGGAG AAGAGCAACA
GCCATACTCA
GAAAAGCAAC CAGGAGATTG ATTCAGCTGA TAGTGAGTGG
GAGAGACGAA
CAGTCGATTG CCGAAGCAAT AATTGTGGCC ATGGTATTTT
CACAAGAGGA
TTGTATGATA AAAGCAGTCA GAGGTGATCT GAATTTCGTC
AATAGGGCGA
ATCAACGATT GAATCCTATG CATCAACTTT AAGACATTT
TCAGAAGGAT
GCGAAAGTGC TTTTTCAAAA TTGGGGAGTT GAACCTATCG
ACAATGTGAT
GGGAATGATT GGGATATTGC CCGACATGAC TCCAAGCATC
GAGATGTCAA
TGAGAGGAGT GAGAATCAGC AAAATGGGTG TAGATGAGTA
CTCCAGCACG
GAGAGGGTAG TGGTGAGCAT TGACCGTTTT TTGAGAATCC
GGGACCAACG
AGGAAATGTA CTACTGTCTC CCGAGGAGGT CAGTGAAACA
CAGGGAACAG
AGAAACTGAC AATAACTTAC TCATCGTCAA TGATGTGGGA
GATTAATGGT
CCTGAATCAG TGTTGGTCAA TACCTATCAA TGGATCATCA
GAAACTGGGA
AACTGTTAAA ATTCAGTGGT CCCAGAACCC TACAATGCTA
TACAATAAAA
TGGAATTTGA ACCATTTCAG TCTTTAGTAC CTAAGGCCAT
TAGAGGCCAA
TACAGTGGGT TTGTAAGAAC TCTGTTCCAA CAAATGAGGG
ATGTGCTTGG
GACATTTGAT ACCGCACAGA TAATAAAACT TCTTCCCTTC
GCAGCCGCTC
CACCAAAGCA AAGTAGAATG CAGTTCTCCT CATTTACTGT
GAATGTGAGG
GGATCAGGAA TGAGAATACT TGTAAGGGGC AATTCTCCTG
TATTCAACTA
TAACAAGGCC ACGAAGAGAC TCACAGTTCT CGGAAAGGAT
GCTGGCACTT
TAACTGAAGA CCCAGATGAA GGCACAGCTG GAGTGGAGTC
CGCTGTTCTG
AGGGGATTCC TCATTCTGGG CAAAGAAGAC AAGAGATATG
GGCCAGCACT
AAGCATCAAT GAACTGAGCA ACCTTGCGAA AGGAGAGAAG
GCTAATGTGC
TAATTGGGCA AGGAGACGTG GTGTTGGTAA TGAAACGGAA
ACGGGACTCT
AGCATACTTA CTGACAGCCA GACAGCGACC AAAAGAATTC
GGATGGCCAT
CAATTAGTGT CGAATAGTTT AAAAACGACC TTGTTTCTAC
T
NP
                                    (SEQ ID NO:4)
AGCAAAAGCA GGGTAGATAA TCACTCACTG AGTGACATCA
AAATCATGGC GTCTCAAGGC ACCAAACGAT CTTACGAACA
```

```
GATGGAGACT
GATGGAGAAC GCCAGAATGC CACTGAAATC AGAGCATCCG
TCGGAAAAAT
GATTGGTGGA ATTGGACGAT TCTACATCCA AATGTGCACC
GAACTCAAAC
TCAGTGATTA TGAGGGACGG TTGATCCAAA ACAGCTTAAC
AATAGAGAGA
ATGGTGCTCT CTGCTTTTGA CGAAAGGAGA AATAAATACC
TTGAAGAACA
TCCCAGTGCG GGGAAAGATC CTAAGAAAAC TGGAGGACCT
ATATACAGGA
GAGTAAACGG AAAGTGGATG AGAGAACTCA TCCTTTATGA
CAAAGAAGAA
ATAAGGCGAA TCTGGCGCCA AGCTAATAAT GGTGACGATG
CAACGGCTGG
TCTGACTCAC ATGATGATCT GGCATTCCAA TTTGAATGAT
GCAACTTATC
AGAGGACAAG AGCTCTTGTT CGCACCGGAA TGGATCCCAG
GATGTGCTCT
CTGATGCAAG GTTCAACTCT CCCTAGGAGG TCTGGAGCCG
CAGGTGCTGC
AGTCAAAGGA GTTGGAACAA TGGTGATGGA ATTGGTCAGA
ATGATCAAAC
GTGGGATCAA TGATCGGAAC TTCTGGAGGG GTGAGAATGG
ACGAAAAACA
AGAATTGCTT ATGAAAGAAT GTGCAACATT CTCAAAGGGA
AATTTCAAAC
TGCTGCACAA AAAGCAATGA TGGATCAAGT GAGAGAGAGC
CGGAACCCAG
GGAATGCTGA GTTCGAAGAT CTCACTTTTC TAGCACGGTC
TGCACTCATA
TTGAGAGGGT CGGTTGCTCA CAAGTCCTGC CTGCCTGCCT
GTGTGTATGG
ACCTGCCGTA GCCAGTGGGT ACGACTTTGA AAGGGAGGGA
TACTCTCTAG
TCGGAATAGA CCCTTTCAGA CTGCTTCAAA ACAGCCAAGT
GTACAGCCTA
ATCAGACCAA ATGAGAATCC AGCACACAAG AGTCAACTGG
TGTGGATGGC
ATGCCATTCT GCCGCATTTG AAGATCTAAG AGTATTAAGC
TTCATCAAAG
GGACGAAGGT GCTCCCAAGA GGGAAGCTTT CCACTAGAGG
AGTTCAAATT
GCTTCCAATG AAAATATGGA GACTATGGAA TCAAGTACAC
TTGAACTGAG
AAGCAGGTAC TGGGCCATAA GGACCAGAAG TGGAGGAAAC
ACCAATCAAC
AGAGGGCATC TGCGGGCCAA ATCAGCATAC AACCTACGTT
CTCAGTACAG
AGAAATCTCC CTTTTGACAG AACAACCATT ATGGCAGCAT
TCAATGGGAA
TACAGAGGGG AGAACATCTG ACATGAGGAC CGAAATCATA
AGGATGATGG
AAAGTGCAAG ACCAGAAGAT GTGTCTTTCC AGGGGCGGGG
AGTCTTCGAG
CTCTCGGACG AAAAGGCAGC GAGCCCGATC GTGCCTTCCT
TTGACATGAG
TAATGAAGGA TCTTATTTCT TCGGAGACAA TGCAGAGGAG
TACGACAATT
AAAGAAAAAT ACCCTTGTTT CTACT
M                                     (SEQ ID NO:5)
AGCAAAAGCA GGTAGATATT GAAAGATGAG TCTTCTAACC
GAGGTCGAAA
CGTACGTACT CTCTATCATC CCGTCAGGCC CCCTCAAAGC
CGAGATCGCA
CAGAGACTTG AAGATGTCTT TGCAGGGAAG AACACCGATC
TTGAGGTTCT
CATGGAATGG CTAAAGACAA GACCAATCCT GTCACCTCTG
ACTAAGGGGA
TTTTAGGATT TGTGTTCACG CTCACCGTGC CCAGTGAGCG
AGGACTGCAG
CGTAGACGCT TTGTCCAAAA TGCCCTTAAT GGGAACGGGG
ATCCAAATAA
CATGGACAAA GCAGTTAAAC TGTATAGGAA GCTCAAGAGG
GAGATAACAT
TCCATGGGGC CAAAGAAATC TCACTCAGTT ATTCTGCTGG
TGCACTTGCC
AGTTGTATGG GCCTCATATA CAACAGGATG GGGGCTGTGA
CCACTGAAGT
GGCATTTGGC CTGGTATGTG CAACCTGTGA ACAGATTGCT
GACTCCCAGC
```

```
ATCGGTCTCA TAGGCAAATG GTGACAACAA CCAATCCACT
AATCAGACAT
GAGAACAGAA TGGTTTTAGC CAGCACTACA GCTAAGGCTA
TGGAGCAAAT
GGCTGGATCG AGTGAGCAAG CAGCAGAGGC CATGGAGGTT
GCTAGTCAGG
CTAGACAAAT GGTGCAAGCG ATGAGAACCA TTGGGACTCA
TCCTAGCTCC
AGTGCTGGTC TGAAAAATGA TCTTCTTGAA AATTTGCAGG
CCTATCAGAA
ACGAATGGGG GTGCAGATGC AACGGTTCAA GTGATCCTCT
CACTATTGCC
GCAAATATCA TTGGGATCTT GCACTTGACA TTGTGGATTC
TTGATCGTCT
TTTTTTCAAA TGCATTTACC GTCGCTTTAA ATACGGACTG
AAAGGAGGGC
CTTCTACGGA AGGAGTGCCA AAGTCTATGA GGGAAGAATA
TCGAAAGGAA
CAGCAGAGTG CTGTGGATGC TGACGATGGT CATTTTGTCA
GCATAGAGCT
GGAGTAAAAA ACTACCTTGT TTCTACT
NS
                                    (SEQ ID NO:6)
AGCAAAAGCA GGGTGACAAA AACATAATGG ATCCAAACAC
TGTGTCAAGC
TTTCAGGTAG ATTGCTTTCT TTGGCATGTC CGCAAACGAG
TTGCAGACCA
AGAACTAGGC GATGCCCCAT TCCTTGATCG GCTTCGCCGA
GATCAGAAAT
CCCTAAGAGG AAGGGGCAGT ACTCTCGGTC TGGACATCAA
GACAGCCACA
CGTGCTGGAA AGCAGATAGT GGAGCGGATT CTGAAAGAAG
AATCCGATGA
GGCACTTAAA ATGACCATGG CCTCTGTACC TGCGTCGCGT
TACCTAACTG
ACATGACTCT TGAGGAAATG TCAAGGGACT GGTCCATGCT
CATACCCAAG
CAGAAAGTGG CAGGCCCTCT TTGTATCAGA ATGGACCAGG
CGATCATGGA
TAAGAACATC ATACTGAAAG CGAACTTCAG TGTGATTTTT
GACCGGCTGG
AGACTCTAAT ATTGCTAAGG GCTTTCACCG AAGAGGGAGC
AATTGTTGGC
GAAATTTCAC CATTGCCTTC TCTTCCAGGA CATACTGCTG
AGGATGTCAA
AAATGCAGTT GGAGTCCTCA TCGGAGGACT TGAATGGAAT
GATAACACAG
TTCGAGTCTC TGAAACTCTA CAGAGATTCG CTTGGAGAAG
CAGTAATGAG
AATGGGAGAC CTCCACTCAC TCCAAAACAG AAACGAGAAA
TGGCGGGAAC
AATTAGGTCA GAAGTTTGAA GAAATAAGAT GGTTGATTGA
AGAAGTGAGA
CACAAACTGA AGATAACAGA GAATAGTTTT GAGCAAATAA
CATTTATGCA
AGCCTTACAT CTATTGCTTG AAGTGGAGCA AGAGATAAGA
ACTTTCTCGT
TTCAGCTTAT TTAGTACTAA AAACACCCT TGTTTCTACT
HA
                                    (SEQ ID NO:7)
AGCAAAAGCAGGGGAAAATAAAAACAACCAAAATGAGGCAAACCTACTGG
TCCTGTTATGTGCACTTGCAGCTGCAGAT
GCAGACACAATATGTATAGGCTACCATGCGAACAATTCAACCGACACTGT
TGACACAGTACTCGAGAAGAATGTGACAGT
GACACACTCTGTTAACCTGCTCGAAGACAGCCACAACGGAAAACTATGTA
GATTAAAAGGAATAGCCCCACTACAATTGG
GGAAATGTAACATCGCCGGATGGCTCTTGGGAAACCCAGAATGCGACCCA
CTGCTTCCAGTGAGATCATGGTCCTACATT
GTAGAAACACCAAACTCTGAGAATGGAATATGTTATCCAGGAGATTTCAT
CGACTATGAGGAGCTGAGGGAGCAATTGAG
CTCAGTGTCATCATTCGAAAGATTCGAAATATTTCCCAAAGAAAGCTCAT
GGCCCAACCACAACACAAACGGAGTAACGG
CAGCATGCTCCCATGAGGGGAAAAGCAGTTTTTACAGAAATTTGCTATGG
CTGACGGAGAAGGAGGGCTCATACCCAAAG
CTGAAAAATTCTTATGTGAACAAAAAGGGAAAGAAGTCCTTGTACTGTG
GGGTATTCATCACCCGCCTAACAGTAAGGA
ACAACAGAATCTCTATCAGAATGAAAATGCTTATGTCTCTGTAGTGACTT
CAAATTATAACAGGAGATTTACCCCGGAAA
TAGCAGAAAGACCCAAAGTAAGAGATCAAGCTGGGAGGATGAACTATTAC
TGGACCTTGCTAAAACCCGGAGACACAATA
ATATTTGAGGCAAATGGAAATCTAATAGCACCAATGTATGCTTTCGCACT
GAGTAGAGGCTTTGGGTCCGGCATCATCAC
CTCAAACGCATCAATGCATGAGTGTAACACGAAGTGTCAAACACCCCTGG
```

-continued
GAGCTATAAACAGCAGTCTCCCTTACCAGA

ATATACACCCAGTCACAATAGGAGAGTGCCCAAAATACGTCAGGAGTGCC

AAATTGAGGATGGTTACAGGACTAAGGAAC

ATTCCGTCCATTCAATCCAGAGGTCTATTTGGAGCCATTGCCGGTTTTAT

TGAAGGGGATGGACTGGAATGATAGATGG

ATGGTATGGTTATCATCATCAGAATGAACAGGGATCAGGCTATGCAGCGG

ATCAAAAAGCACACAAAATGCCATTAACG

GGATTACAAACAAGGTGAACACTGTTATCGAGAAAATGAACATTCAATTC

ACAGCTGTGGGTAAAGAATTCAACAAATTA

GAAAAAAGGATGGAAATTTAAATAAAAAAGTTGATGATGGATTTCTGGA

CATTTGGACATATAATGCAGAATTGTTAGT

TCTACTGGAAAATGAAAGGACTCTGGATTTCCATGACTCAAATGTGAAGA

ATCTGTATGAGAAAGTAAAAAGCCAATTAA

AGAATAATGCCAAAGAAATCGGAAATGGATGTTTTGAGTTCTACCACAAG

TGTGACAATGAATGCATGGAAAGTGTAAGA

AATGGGACTTATGATTATCCCAAATATTCAGAAGAGTCAAAGTTGAACAG

GGAAAAGGTAGATGGAGTGAAATTGGAATC

AATGGGGATCTATCAGATTCTGGCGATCTACTCAACTGTCGCCAGTTCAC

TGGTGCTTTTGGTCTCCCTGGGGGCAATCA

GTTTCTGGATGTGTTCTAATGGATCTTTGCAGTGCAGAATATGCATCTGA

GATTAGAATTTCAGAGATATGAGGAAAAAC

ACCCTTGTTTCTACT

NA (SEQ ID NO:8)
AGCAAAAGCAGGGGTTTAAAATGAATCCAAATCAGAAAATAATAACCATT

GGATCAATCTGTCTGGTAGTCGGACTAATT

AGCCTAATATTGCAAATAGGGAATATAATCTCAATATGGATTAGCCATTC

AATTCAAACTGGAAGTCAAAACCATACTGG

AATATGCAACCAAAACATCATTACCTATAAAAATAGCACCTGGGTAAAGG

ACACAACTTCAGTGATATTAACCGGCAATT

CATCTCTTTGTCCCATCCGTGGGTGGGCTATATACAGCAAAGACAATAGC

ATAAGAATTGGTTCCAAAGGAGACGTTTTT

GTCATAAGAGAGCCCTTTATTTCATGTTCTCACTTGGAATGCAGGACCTT

TTTTCTGACCCAAGGTGCCTTACTGAATGA

CAAGCATTCAAGTGGGACTGTTAAGGACAGAAGCCCTTATAGGGCCTTAA

TGAGCTGCCCTGTCGGTGAAGCTCCGTCCC

CGTACAATTCAAGATTTGAATCGGTTGCTTGGTCAGCAAGTGCATGTCAT

GATGGCATGGGCTGGCTAACAATCGGAATT

TCAGGTCCAGATAATGGAGCAGTGGCTGTATTAAAATACAACGGCATAAT

AACTGAAACCATAAAAAGTTGGAGGAAGAA

AATATTGAGGACACAAGAGTCTGAATGTGCCTGTGTAAATGGTTCATGTT

TTACTATAATGACTGATGGCCCGAGTGATG

GGCTGGCCTCGTACAAAATTTTCAAGATCGAAAAGGGGAAGGTTACTAAA

TCAATAGAGTTGAATGCACCTAATTCTCAC

TATGAGGAATGTTCCTGTTACCCTGATACCGGCAAAGTGATGTGTGTGTG

CAGAGACAATTGGCATGGTTCGAACCGGCC

ATGGGTGTCTTTCGATCAAAACCTGGATTATCAAATAGGATACATCTGCA

GTGGGGTTTTCGGTGACAACCCGCGTCCCG

AAGATGGAACAGGCAGCTGTGGTCCAGTGTATGTTGATGGAGCAAACGGA

GTAAAGGGATTTTCATATAGGTATGGTAAT

GGTGTTTGGATAGGAAGGACCAAAAGTCACAGTTCCAGACATGGGTTTGA

GATGATTTGGGATCCTAATGGATGGACAGA

GACTGATAGTAAGTTCTCTGTGAGGCAAGATGTTGTGGCAATGACTGATT

GGTCAGGGTATAGCGGAAGTTTCGTTCAAC

ATCCTGAGCTGACAGGGCTAGACTGTATGAGGCCGTGCTTCTGGGTTGAA

TTAATCAGGGGACGACCTAAAGAAAAAACA

ATCTGGACTAGTGCGAGCAGCATTTCTTTTTGTGGCGTGAATAGTGATAC

TGTAGATTGGTCTTGGCCAGACGGTGCTGA

GTTGCCATTCAGCATTGACAAGTAGTCTGTTCAAAAAACTCCTTGTTTCT

ACT

EXAMPLE 2

Influenza virus A/Hong Kong/213/2003 (H5N1, HK213) replicates systemically in chickens, causing lethal infection. Furthermore, this virus is lethal to chicken embryos. Thus, although its surface proteins are highly related to the currently circulating pathogenic avian influenza viruses, HK213 cannot be used as a vaccine strain as attempts to grow it in embryonated chicken eggs result in the production of poor-quality allantoic fluid. Additionally, the use of this highly virulent virus in the production of vaccines is unsafe for vaccine workers. To test the feasibility of using AIPR/8/34 as a master vaccine strain, the cleavage site of the hemagglutinin (HA) gene of HK213 (containing multiple basic amino acids) was mutated from a virulent to an avirulent phenotype (from RERRRKKR (SEQ ID NO:29) to - - - TETR (SEQ ID NO:30)). A virus containing the mutated HA gene produced non-lethal, localized infection in chickens. Additionally, the mutated virus was non-lethal to chicken embryos. Thus, growth of the mutated virus in embronated eggs yielded high-quality allantoic fluid, and in this attenuated form, the virus is safe for vaccine producers.

A recombinant virus containing the neuraminidase (NA) and mutated HA genes from HK213, and all the remaining genes from high-titer A/PR/8/34 (H1N1, HG-PR8) virus (Example 1), which grows 10 times better than other A/PR/8/34 PR8 strains in eggs ($10^{10}$ $EID_{50}$/ml; HA titer: 1:8,000), was generated in embryonated chicken eggs. This recombinant virus, which expresses surface proteins related to the currently circulating pathogenic avian influenza virus, grew to high titers in embryonated chicken eggs (FIG. 1). Thus, replacement of the HA and NA genes of HG-PR8 with those of a currently circulating strain of influenza virus resulted in a vaccine strain that can be safely produced, and demonstrates the use of PR8-HG as a master vaccine strain.

EXAMPLE 3

In Hong Kong in 1997, a highly pathogenic H5N1 avian influenza virus was transmitted directly from birds to humans, causing 18 confirmed infections and 6 deaths (Subbarao et al., 1998; Claas et al., 1998). In 2004-6, the geographic distribution of H5N1 viruses expanded in Asia, spreading to several adjacent European countries and to Africa. Altogether, 96 people infected with the virus have died in Vietnam, Thailand, Cambodia, Indonesia, China, Turkey, and Iraq (Li et al., 2004; WHO). These fatal outbreaks and the continued threat of a pandemic have led to the development of H5N1 virus vaccines for use in humans. However, because pathogenic H5N1 viruses grow poorly in embryonated chicken eggs and pose serious biosafety concerns for vaccine producers, reverse genetics has been used to generate vaccine candidates (Subbarao et al., 2003; Webby et al., 2004; Stephanson et al., 2004; Wood & Robertson, 2004).

Recombinant (6:2 reassortant) viruses that possess modified avirulent-type hemagglutinin (HA) and neuraminidase (NA) genes, both derived from a pathogenic H5N1 strain, with all remaining genes from a donor virus that grows well in eggs, are among the candidates to be produced by this method. The World Health Organization (WHO) recommends A/Puerto Rico/8/34 (H1N1; PR8) as a donor virus, because of its safety in humans and vigorous growth in eggs (Wood & Robertson, 2004; Webby & Webster, 2003). Recently, it was shown that such recombinant viruses grow less well in eggs than does the wild-type PR8 strain, even though they possess the same PR8 "internal" genes (i.e., those other than the HA and NA) (Horimoto et al., 2006).

Since vigorous growth in eggs is an essential property of vaccine seed viruses used in the production of inactivated vaccines, as described below, H5N1 vaccine candidates were generated that grow as well as the PR8 donor strain in eggs. First, the molecular basis for the high growth of PR8 in eggs was determined by defining the genes responsible for this property using reassortment analysis between PR8 and a WSN strain that grows poorly in eggs. It was found that HA-NA balance and PB1 function are important growth determinants. With this knowledge, a series of H5N1 viruses was produced with altered HA-NA combinations, with the PR8 background, to assess their growth in eggs against more conventional 6:2 reassortants, including the WHO-recommended NIBRG-14 virus.

Methods

Cells and Viruses 293T human embryonic kidney cells were maintained in Dulbecco's modified Eagle's minimal essential medium (DMEM) with 10% fetal calf serum and antibiotics. Madin-Darby canine kidney (MDCK) cells were grown in MEM with 5% newborn calf serum and antibiotics. African green monkey Vero WCB cells, which had been established after biosafety tests for use in human vaccine production (Sugawara et al., 2002), were maintained in serum-free VP-SFM medium (GIBCO-BRL) with antibiotics. Cells were maintained at 37° C. in 5% $CO_2$. The A/Vietnam/1194/2004 and A/Vietnam/1203/2004 (H5N1; VN1194 and VN1203) strains, isolated from humans, were propagated in 10-day-old embryonated chicken eggs for 2 days at 37° C., after which time the allantoic fluids containing virus were harvested and used for further experiments. All experiments with these viruses were carried out in a Biosafety Level 3 containment laboratory. The WHO-recommended vaccine seed virus, NIBRG-14 (VN1194/PR8 6:2 reassortant virus), was kindly gifted by Drs. John Wood and Jim Robertson at the National Institute for Biological Standards and Control, UK.

Construction of Plasmids and Reverse Genetics

To generate reassortants of influenza A viruses, a plasmid-based reverse genetics (Neumann et al., 1999) was used. Viral RNA from VN1194 or VN1203 was extracted from allantoic fluid by using a commercial kit (ISOGEN LS, Nippon Gene) and was converted to cDNA by using reverse transcriptase (SuperScript III; GIBCO-BRL) and primers containing the consensus sequences of the 3' ends of the RNA segments for the H5 viruses. The full-length cDNAs were then PCR-amplified with ProofStart polymerase (QIAGEN) and H5 subtype-specific primer pairs, and cloned into a plasmid under control of the human polymerase I promoter and the mouse RNA polymerase I terminator (PolI plasmids), generating a PolI-VN1194/HA or a PolI-VN1203/HA construct containing the VN1194 or VN1203 HA gene, respectively. By inverse PCR using back-to-back primer pairs, followed by ligation, the HA cleavage site sequence of the wild-type VN1194 or VN1203 (RERRRKKR; SEQ ID NO:29) virus was altered to create the avirulent-type sequence (RETR; SEQ ID NO:3 1) as described in Horimoto et al. (2006), the disclosure of which is incorporated by reference herein. A PolI-VN1203NA containing the VN1203 NA gene was constructed by the RT-PCR procedure (described above) with N1-specific primers. A series of pPolI NA mutant plasmids were prepared by inverse PCR. Using the PolI-VN1203NA as a template, pPolI-NAfill was constructed, which encodes a mutant NA containing a 20-amino acid (aa) (CNQSIITY-ENNTWVNQTYVN; SEQ ID NO:32) insertion derived from A/goose/Guangdong/1/96 (H5N1; GsGd96) NA into the NA stalk between 48-Pro and 49-Ile. pPolI-NAfill.N2 and -NAfill.N2N9, in which N2 (12 aa) or N2+N9 (12+12 aa) sequences derived from the stalk region of each NA subtype were inserted into the NA stalk between 42-Asn and 43-Gln, were constructed as described in Castrucci et al. (1993). All of these constructs were sequenced to ensure the absence of unwanted mutations.

A previously produced series of PolI constructs, derived from A/WSN/33 (H5N1; WSN) and PR8 strains was used, for reverse genetics (Horimoto et al., 2006; Neumann et al., 1999). Additionally, PolI constructs containing NA genes derived from A/Hong Kong/213/03 (H5N1; HK213), and A/Kanagawa/173/2001 (H1N1; Kanagawa) were used in this study (Horimoto et al., 2006; Kobasa et al., 2004; Peiris et al., 2004).

Plasmids expressing WSN or PR8 NP, PA, PB1, or PB2 under control of the chicken β-actin promoter were used for all reverse genetics experiments (Horimoto et al., 2006; Neumann et al., 1999). Briefly, PolI plasmids and protein expression plasmids were mixed with a transfection reagent, Trans-IT 293T (Panvera), incubated at room temperature for 15 min, and then added to 293T cells. Transfected cells were incubated in Opti-MEM I (GIBCO-BRL) for 48 hours. For reverse genetics in Vero WCB cells, an electroporator (Amaxa) was used to transfect the plasmid mixtures according to the manufacturer's instructions. Sixteen hours after transfection, freshly prepared Vero WCB cells were added onto the transfected cells and TPCK-trypsin (1 μg/ml) was added to the culture 6 hours later. Transfected cells were incubated in serum-free VP-SFM for a total of 4 days. Supernatants containing infectious viruses were harvested, biologically cloned by limiting dilution in embryonated eggs, and used in further experiments.

Properties of Viral Replication in Eggs

Virus was inoculated into the allantoic cavity of 10-day-old embryonated chicken eggs, and incubated at 37° C. for 48 hours. Virus in the allantoic fluids was then titrated by HA assay using either 0.5% chicken erythrocytes or 0.8% guinea pig erythrocytes or in eggs to determine the median egg infectious dose ($EID_{50}$)/ml of virus. For some viruses, plaque titration was conducted with MDCK cells and TPCK-trypsin (1 μg/ml). The growth kinetics of some viruses was assessed in eggs after inoculating $10^4$ $EID_{50}$ of virus.

Virus Elution Assay from Chicken Erythrocytes

Fifty μl of twofold dilutions of virus containing the HA titers of 1:1024 were incubated with 50 μl of 0.5% chicken erythrocytes in a microtiter plate at 4° C. for 1 hour. The plate was then stored at 37° C., and the reduction of HA titers was recorded periodically. Phosphate-buffered saline with 6.8 mM $CaCl_2$ was used as a diluent.

Results

Molecular Basis for the High Growth Property of PR8 in Chicken Eggs

Although PR8 is recommended by WHO for use as a donor virus to generate reverse genetics-based H5 influenza vaccine, the molecular basis of its high growth property is not fully understood. The M gene was said to be responsible for the vigorous growth of PR8 in eggs (Subbarao et al., 2003), but this claim is apparently not found in the published original data (Kilbourne et al., 1969). Thus, a reassortment analysis was conducted using a WSN strain that grows poorly in eggs. Table 3 shows the compatibility between the HAs and NAs of PR8 versus the WSN strain in terms of viral growth in embryonated chicken eggs. All reassortant test viruses grew better than the wild-type WSN, but less well than the egg-adapted PR8, demonstrating that both surface glycoproteins and internal proteins are responsible for the high growth property of PR8.

TABLE 3

Compatibility between the HAs and NAs of PR8 versus WSN strains, assessed by viral growth in chicken embryonated eggs

| Gene constellation of reassortant | | | HA titer[b] | |
|---|---|---|---|---|
| HA | NA | 6 others[a] | Chicken RBC | Guinea pig RBC |
| WSN | WSN | WSN | 16/8 | 32/8 |
| PR8 | WSN | WSN | 64/32 | 64/32 |
| WSN | PR8 | WSN | 16/16 | 32/16 |
| PR8 | PR8 | WSN | 128/128 | 128/128 |
| WSN | WSN | PR8 | 64/64 | 64/64 |
| PR8 | WSN | PR8 | 64/128 | 64/128 |
| WSN | PR8 | PR8 | 512/512 | 512/512 |
| PR8 | PR8 | PR8 | 2048/2048 | 2048/2048 |

[a]Genes encoding the internal proteins PB1, PB2, PA, NP, M, and NS.
[b]Growth of each reassortant virus in chicken eggs, assessed in HA assays with 0.5% chicken RBC and 0.8% guinea pig RBC. HA titers from two independent experiments are shown.

Since the growth of a reassortant virus containing both of the PR8 glycoproteins and all six internal proteins derived from WSN was drastically reduced in eggs, as compared with that of PR8 (Tables 3 and 4), a series of reassortant viruses was produced to define the internal proteins responsible for this property. A single-gene reassortant virus containing the WSN PB1 and all remaining genes from PR8 grew poorly, at a level similar to that of a reassortant containing all of the WSN genes encoding internal proteins, whereas a reassortant containing the PR8 PB1 and WSN genes encoding all remaining internal proteins replicated to a high titer (Table 4). Thus, the PR8 PB1 likely possesses the optimal polymerase activity for viral genome replication in eggs, in contrast to a previous report implicating the M segment in this role (Subbarao et al., 2003). Table 4 Compatibility among genes encoding internal proteins of PR8 and WSN viruses, assessed by viral growth in chicken embryonated eggs

| Gene constellation of reassortant[a] | | | | | | | | HA titer[b] |
|---|---|---|---|---|---|---|---|---|
| HA | NA | PB2 | PB1 | PA | NP | M | NS | |
| PR8 | PR8 | PR8 | PR8 | PR8 | PR8 | PR8 | PR8 | 2048/2048/1024 |
| PR8 | PR8 | PR8 | PR8 | PR8 | PR8 | PR8 | WSN | 1024/1024/1024 |
| PR8 | PR8 | PR8 | PR8 | PR8 | PR8 | WSN | PR8 | 2048/1024/1024 |
| PR8 | PR8 | PR8 | PR8 | PR8 | PR8 | WSN | WSN | 1024/1024/512 |
| PR8 | PR8 | PR8 | PR8 | PR8 | WSN | PR8 | PR8 | 1024/1024/512 |
| PR8 | PR8 | PR8 | PR8 | WSN | PR8 | PR8 | PR8 | 1024/512/256 |
| PR8 | PR8 | PR8 | WSN | PR8 | PR8 | PR8 | PR8 | 128/64/64 |
| PR8 | PR8 | WSN | PR8 | PR8 | PR8 | PR8 | PR8 | 1024/1024/1024 |
| PR8 | PR8 | WSN | WSN | WSN | WSN | PR8 | PR8 | 64/64/32 |
| PR8 | PR8 | WSN | WSN | WSN | WSN | WSN | WSN | 128/64/64 |
| PR8 | PR8 | WSN | PR8 | WSN | WSN | WSN | WSN | 1024/512/512 |

[a]Both the HA and NA genes were derived from PR8 in all reassortant viruses, while some of the genes encoding internal proteins were from the WSN strain.
[b]Growth rate of each reassortant virus in chicken eggs was assessed with HA assays in 0.5% chicken RBC. HA titers, obtained in three independent experiments, are shown.

Figure 2:
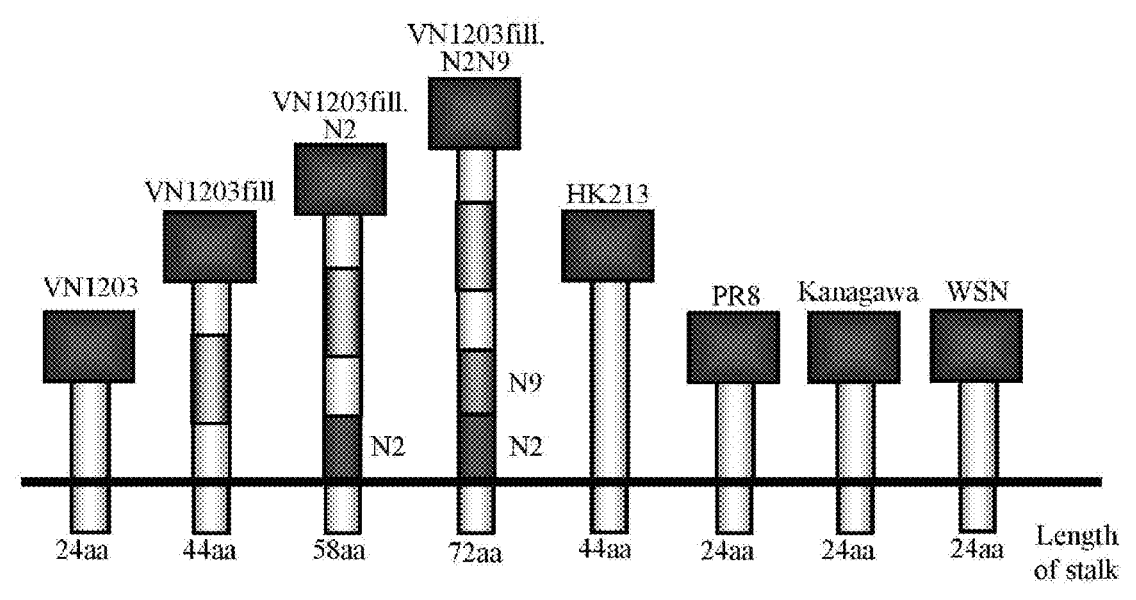

Generation of H5N1 Vaccine Seed Candidates with Enhanced Growth Ability in Chicken Eggs In an earlier study, the growth of WSN in eggs was shown to be enhanced by lengthening the NA stalk to increase NA function: the longer the stalk, the better the replication of the virus (Castrucci et al., 1993). This finding prompted the production of a series of H5N1 viruses comprising mutated or heterologous N1s with the PR8 background and compare their growth in eggs. The A/Vietnam/1203/2004 (H5N1; VN1203) NA contains a 20-amino acid (20-aa) deletion in its stalk region (hence, 24 aa in the stalk). Therefore, a mutant NA, VN1203fill, was constructed containing a 44-aa stalk like the H5N1 precursor virus A/goose/Guangdong/1/96 (H5N1) (Xu et al., 1999), as well as other NA mutants, VN1202fill.N2 and VN1203fill.N2N9 that contained longer stalks, 58- and 72-aa, respectively (FIG. 2). The heterologous Ni from A/Hong Kong/213/03 (H5N1; HK213) containing 44-aa in the stalk was also examined. The NAs from H1N1 strains such as PR8, A/Kanagawa/173/2001 (H1N1; Kanagawa), and WSN, all of which possess 24-aa in the stalk, were also tested. Using these NA constructs, a total of eight reassortant viruses was generated, seven 6:2 and one 7:1 with the modified avirulent-type VN1203 HA and PR8 background (Table 5). Another series of reassortant viruses was constructed with the modified avirulent-type A/Vietnam/1194/2004 (H5N1; VN1194) HA. By comparison with constructs containing the parental VN1203 NA, only the 7:1 reassortant virus and a 6:2 reassortant containing a combination of the modified VN1194 HA and VN1203fill NA, showed enhanced growth in eggs.

TABLE 5

Viral titers of H5N1/PR8 reassortant viruses in chicken embryonated eggs[a)]
HA titer/Infectivity titer ($\log_2$/$\log_{10}$EID$_{50}$/ml)

| HA[b)] | Experiment[c)] | VN1203 | VN1203fill | VN1203fill.N2 | NA derived from[d)] VN1203fill.N2N9 | HK213 | PR8 | Kanagawa | WSN | Wild-type PR8[e)] |
|---|---|---|---|---|---|---|---|---|---|---|
| VN1203 | 1 | 9.2 ± 0.4/ | 9.6 ± 0.5/ | 9.2 ± 0.5/ | 9.0 ± 0.0/ | 9.6 ± 0.5/ | 9.6 ± 0.5/ | 9.8 ± 0.4/ | <1.0/ | 10.7 ± 0.6/ |
| | | 8.9 ± 0.3[f)] | 8.8 ± 0.6 | 8.9 ± 0.4 | 8.8 ± 0.5 | 8.8 ± 0.1 | 9.5 ± 0.4 | 9.4 ± 0.2 | ND | 10.3 ± 0.4 |
| | 2 | 9.0 ± 1.0/ | 9.0 ± 0.0/ | 8.3 ± 0.6/ | 8.0 ± 0.0/ | 8.7 ± 0.6/ | 9.7 ± 0.6/ | ND/ND | ND/ND | 11.0 ± 0.0/ |
| | | 9.4 ± 0.2 | 9.7 ± 0.2 | 8.6 ± 0.2 | ND | 8.5 ± 0.3 | 10.1 ± 0.2 | | | 10.3 ± 0.4 |
| VN1194 | 1 | 8.7 ± 0.6/ | 9.3 ± 0.6/ | 9.3 ± 0.6/ | 9.0 ± 0.0/ | ND/ND | 9.3 ± 0.6/ | 9.0 ± 0.0/ | <1.0/ | 10.7 ± 0.6/ |
| | | 8.7 ± 0.2 | 9.3 ± 0.2 | 9.2 ± 0.2 | 8.6 ± 0.2 | | 9.5 ± 0.3 | 8.8 ± 0.9 | 5.2 ± 0.2 | 10.1 ± 0.2 |

[a)]Eggs (10-day-old) were inoculated with virus ($10^4$EID$_{50}$), and incubated for 48 hours at 37° C.; viral titers in allantoic fluids were determined.
[b)]Two H5 HA genes (VN1203 and VN1194) were used to generate reassortant viruses with a PR8 background. The HA cleavage sites of both VN1203 and VN1194 were modified to that of the avirulent-type H5 HA.
[c)]Two independent experiments, each using 3 to 5 eggs, were performed for VN1203 constructs, while a single experiment was done for VN1194.
[d)]A total of eight NA genes were used to generate reassortant viruses; three insertion mutant NAs (VN1203fill, VN1203fill.N2, and N1203fill.N2N9) were prepared to assess the influence of NA stalk length on virus growth in eggs by comparison to parental VN1203 NA; the other NAs were derived from an H5N1 human isolate (HK213) or H1N1 viruses (PR8, Kanagawa, and WSN). Thus, all reassortant viruses except one containing PR8 NA (7:1 reassortant) are 6:2 reassortantviruses with a PR8 background.
[e)]Growth of wild-type PR8 was also assessed as a control for each experiment.
[f)]Growth of each reassortant virus in eggs was assessed by either HA or infectivity assay, and reported as mean ± s.d. of HA titer ($\log_2$)/mean ± s.d. of infectivity titer ($\log_{10}$EID$_{50}$/ml). Significantly enhanced HA and infectivity titers (p < 0.05, t-test), by comparison to those of standard viruses containing VN1203 HA and VN1203 NA or VN1194 HA and VN1203 NA, are shown in boldface type.
ND, not determined.

Figure 4:
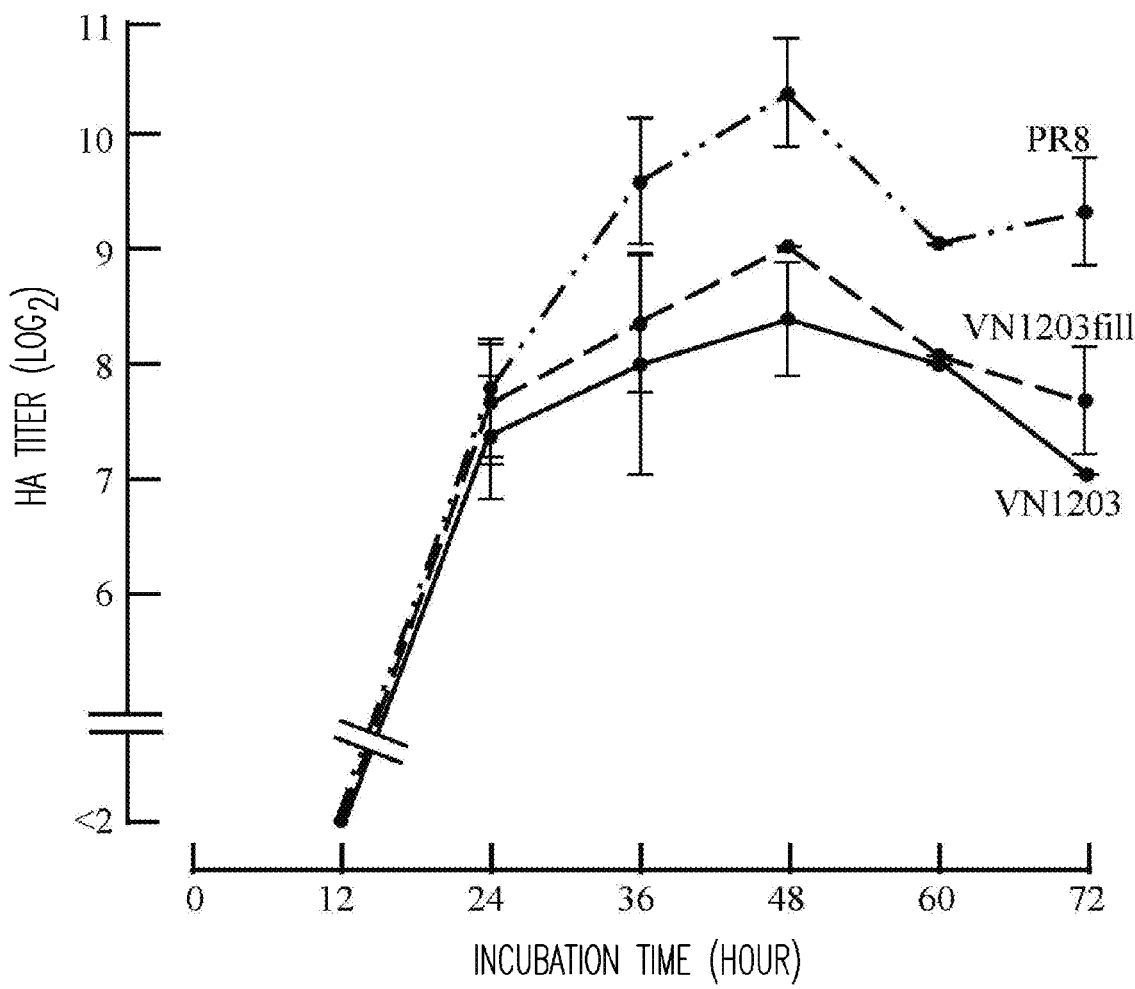
FIG. 4. Growth kinetics of H5N1 reassortant viruses in chicken embryonated eggs. We inoculated eggs with the same amounts ($10^4$ $EID_{50}$) of viruses containing PR8 NA (PR8), VN1203 NA (VN1203), or VN1203fill NA (VN1203fill). Mean HA titers and standard deviations for 3 eggs inoculated with each virus were determined at the indicated time points.

Further testing of selected reassortant viruses by a plaque assay of the stock viruses demonstrated a greater than 3-fold higher titer (p=0.003, Student t-test) for the reassortant virus containing PR8 NA compared with the virus containing parental VN1203 NA, although it did not grow as well as egg-adapted PR8 (FIG. 3). Assessment of the growth kinetics of reassortant viruses with the PR8, VN1203fill or VN1203 NA in eggs revealed a superior growth rate for the virus with PR8 NA (7:1 reassortant) (FIG. 4).

Figure 5:
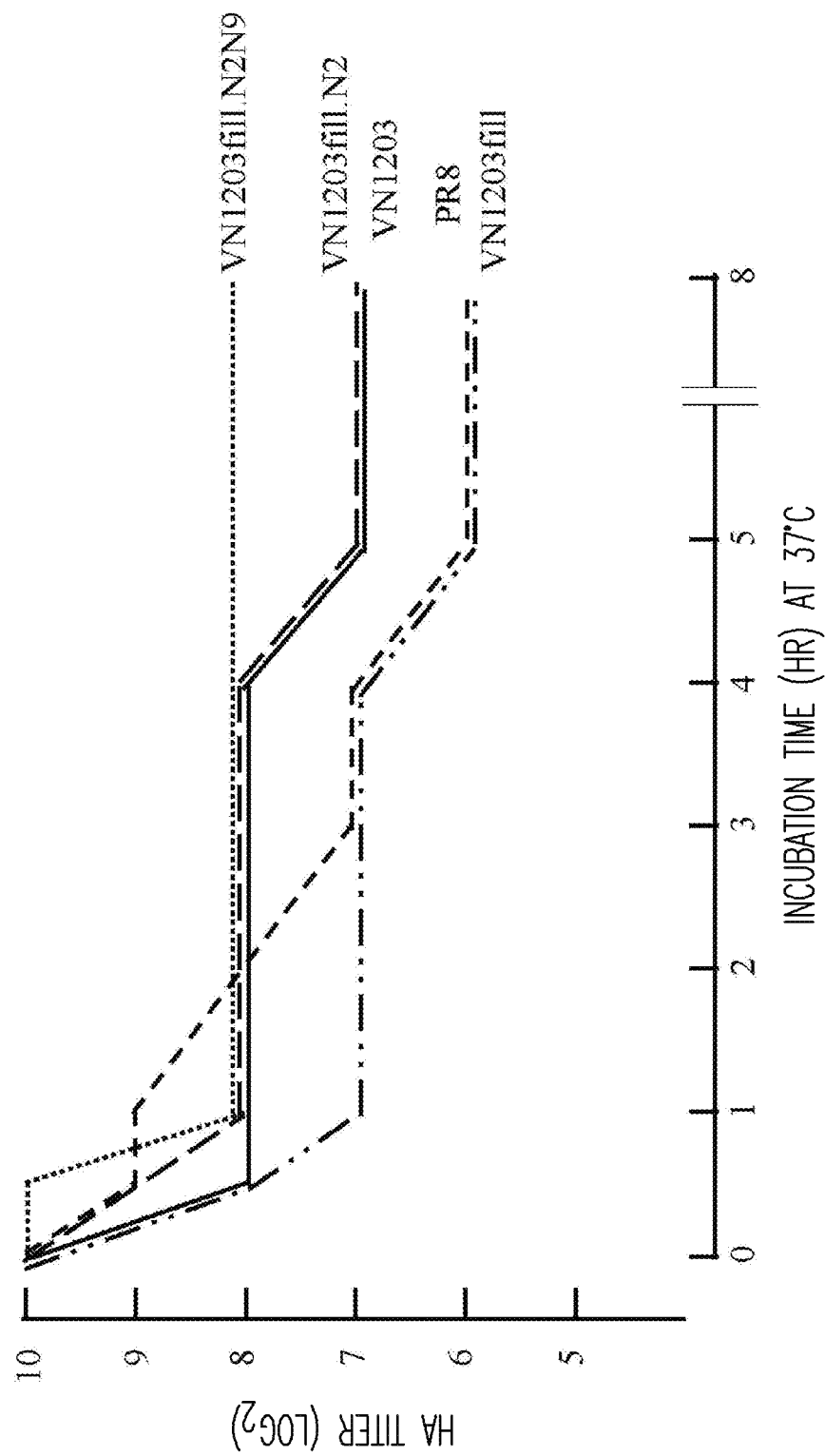
FIG. 5. Virus elution from chicken erythrocytes. Twofold dilutions of each virus (HA titers of 1:1024) containing VN1203 NA with a different stalk length, or PR8 NA, were incubated with chicken erythrocytes in a microtiter plate at 4° C. for 1 hour. The plate was then stored at 37° C. and reductions in the HA titer were recorded for 8 hours.

To determine the molecular basis of the high growth property observed in the 7:1 reassortant virus, the NA function of reassortant viruses was tested by an assay evaluating virus elution from chicken erythrocytes (FIG. 5). Reassortant viruses containing PR8 or VN1203fill NA were eluted from erythrocytes more rapidly than those with the parental VN1203 NA, indicating greater NA activity for PR8 or VN1203fill.NA. These results support the idea that high NA function enhances viral growth in eggs (Castrucci et al., 1993).

Figure 6:
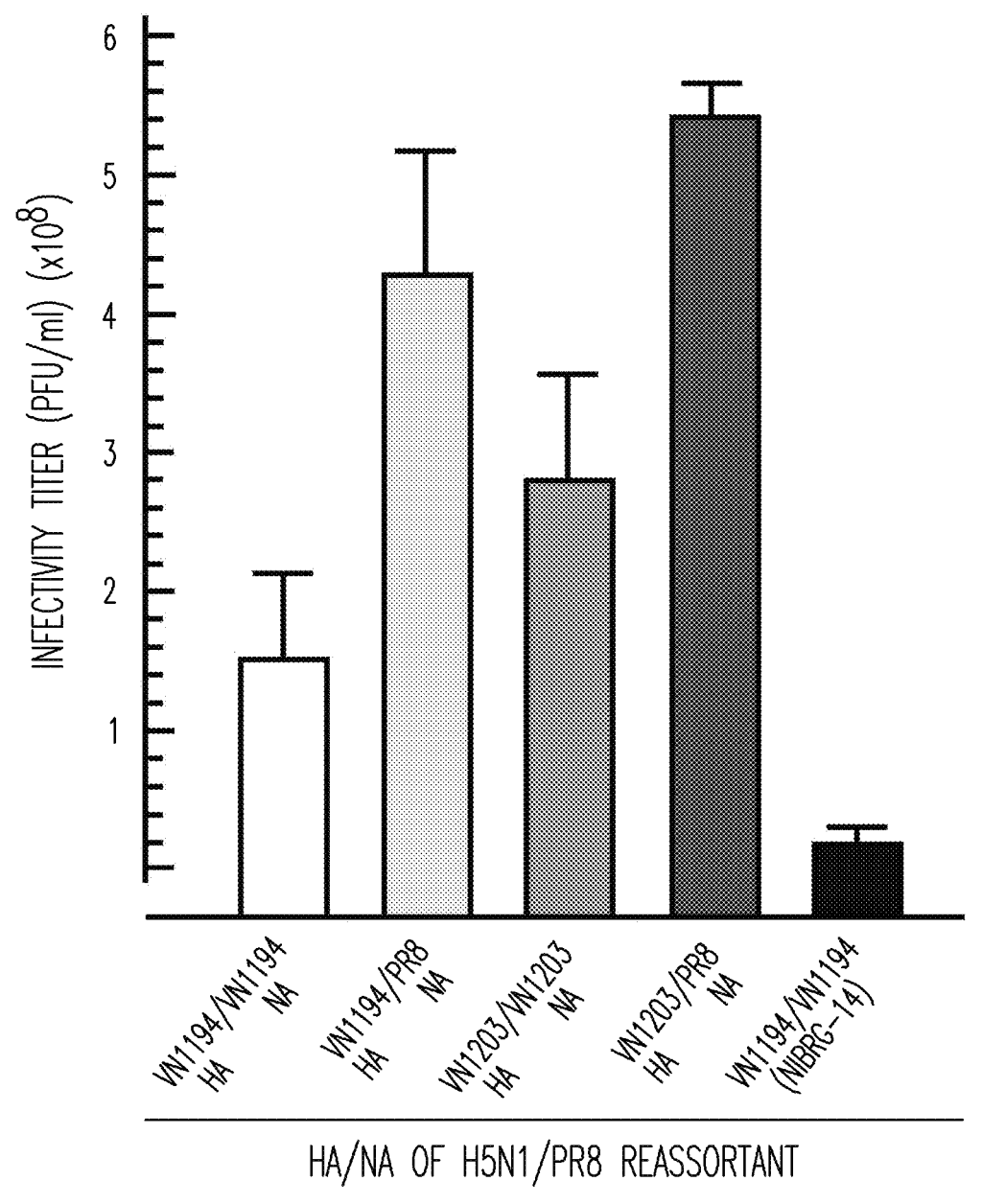

Growth Comparison of H5N1 Vaccine Seed Candidates Produced in this Study with the WHO-Recommended Vaccine Seed Virus, NIBRG-14, in Eggs To validate the potential of candidate seed viruses in the production of H5N1 vaccines, their infectivity titers were compared with that of the WHO-provided NIBRG-14 virus under the same experimental conditions. The 7:1 reassortant viruses containing either VN1194 or VN1203-derived HAs and all the other genes from our PR8 strain showed significantly higher titers (p<0.05, Student t-test) than the NIBRG-14 virus in eggs, as assessed by EID$_{50}$ (Table 6) and plaque titration (FIG. 6). Interestingly, even the 6:2 reassortant virus containing both its HA and NA from the VN1194 virus grew significantly better (about 7-fold, p=0.047) than NIBRG-14 (also a VN1194PR8 6:2 reassortant virus) by plaque titration (FIG. 5). This difference in the growth of two 6:2 reassortant viruses possessing identical VN1194 HAs and NAs indicates that the PR8 strain used in this study would be superior to the one used to generate NIBRG-14 for supporting high viral growth during vaccine production in eggs.

TABLE 6

Growth comparison of H5N1/PR8 reassortant viruses generated in this study with the WHO-recommended vaccine seed virus (NIBRG-14)[a)]

| | Infectivity titer ($\log_{10}$EID$_{50}$/ml) | | | | |
|---|---|---|---|---|---|
| Hours | Reassortants made in this study[b)] | | | | NIBRG-14 |
| Post-infection | VN1194/ VN1194 | VN1194/ PR8 | VN1203/ VN1203 | VN1203/ PR8 | VN1194/ VN1194 |
| 48 | 8.7 ± 0.4 | 9.4 ± 0.2 | 9.1 ± 0.2 | 9.5 ± 0.3 | 8.2 ± 0.3 |
| 60 | 8.3 ± 0.5 | 8.9 ± 0.5 | 8.6 ± 0.4 | 9.2 ± 0.3 | 7.4 ± 0.2 |

[a)]Growth of reassortant viruses was assessed by inoculating eggs (n = 3) with each virus, harvesting allantoic fluid at the indicated times, and determining the EID$_{50}$. The data are shown as mean ± s.d. of infectivity titers ($\log_{10}$EID$_{50}$/ml). Significantly enhanced infectivity titers (p < 0.05, t-test), by comparison with those of NIBRG-14, are shown in boldface type.
[b)]Categorized by the derivation of the HA/NA. The HA cleavage site of both VN1203 and VN1194 were modified to that of the avirulent-type H5 HA.

Discussion

Recombinant viruses possessing modified avirulent-type HA and NA genes, both derived from an H5N1 human isolate, and all remaining genes from the PR8 strain (6:2 reassortant) have been produced and used as seed viruses for inactivated influenza vaccines now being tested in human clinical trials (Wood & Robertson, 2004). Seed strains used in this way must grow well in embryonated eggs. Although egg-adapted PR8 meets this requirement, some 6:2 reassortant viruses, despite containing six internal genes from PR8, do not grow well in eggs (Tables 3 and 5). Here it is demonstrated that the growth of egg-adapted PR8 in chicken eggs is affected by the functional balance of the HA and NA surface glycoproteins.

It is likely that low yields of some 6:2 reassortant viruses with a PR8 background and surface glycoproteins from highly pathogenic avian viruses may result not only from an HA-NA functional imbalance for growth in eggs but also from genetic (and/or functional) incompatibility between the avian surface glycoprotein genes and the internal genes from PR8. Here it is shown that among the internal genes of PR8, PB1 is very important for its high growth in eggs. This information suggests another strategy for reverse genetics-based H5N1 vaccine production; that is, the PB8 PB1 gene alone may be sufficient to generate vigorously growing reassortants for vaccine seed viruses. Thus, by using genes that encode non-PB1 internal proteins from strains other than PR8, one might avoid genetic incompatibility between avian and PR8 viruses. Studies to dissect the molecular basis for the high growth property of PR8 PB1 in eggs would be of considerable interest. One could, for example, analyze the structural and functional differences between the PB1s or PB1-F2s of PR8 and WSN (which differ by 18 and 10 amino acids, respectively; Chen et al., 2004).

The 7:1 reassortant viruses produced in this study replicated significantly better (more than 20-fold by plaque titration) than the WHO-recommended 6:2 reassortant virus NIBRG-14. Even the 6:2 reassortant that was identical to the NIBRG-14 except for the PR8 strain of origin replicated 7-fold better than the recommended virus. These findings suggest that the PR8 strain used in this study may be a superior donor virus for the production of reverse genetics-based pandemic vaccines.

One could argue that the 7:1 reassortant viruses would induce a loss of protective immune response due to antigenic differences in the NA proteins (even though both PR8 and the highly pathogenic viruses contain N1 NAs) (Murphy et al., 1972; Kilbourne et al., 1968; Chen et al., 2000). However, since the HA is the major protective antigen in inactivated vaccines, the higher growth property conferred by the PR8 NA would likely offset the limited antigenic mismatch in this minor protective antigen. In the event of a pandemic caused by a highly pathogenic avian influenza virus, chicken eggs will be in short supply. It is proposed that under such conditions, 7:1 reassortant-based vaccine seed viruses possessing an enhanced growth property in eggs would offer an attractive option for the generation of reverse genetics-based H5 vaccine viruses.

EXAMPLE 4

To identify the genes responsible for the high growth rate of an H5N1 vaccine seed virus in chicken embryonated eggs, the growth of reassortant H5N1 viruses possessing PR8(UW) or PR8(Cambridge) internal genes in chicken embryonated eggs was assessed (FIG. 7). The HA and NA genes of all of the reassortant viruses were derived from A/Vietnam/1194/2002. All other genes were derived from either PR8(UW) or PR8 (Cambridge), which also provided the non-HA and -NA genes of the NIBRG-14 vaccine strain. Higher titers were obtained when the majority of internal genes were from PR8 (UW).

The effect of the M and NS genes on the growth of viruses in chicken embryonated eggs is shown in FIG. 8. For PR8 (UW)/1194-CamM and PR8(UW)/1194-CamNS, the M and NS gene segments, respectively, were derived from PR8 (Cambridge), while the other internal segments came from PR8(UW). The HA and NA segments were derived from A/Vietnam/1194/2004. Highest titers were with the M gene segment of PR8(UW) and the NS gene of PR8 (Cambridge).

The results in FIGS. 7-8 show that the polymerase subunit (PA, PB1, and PB2) and NP genes of PR8(UW) enhanced the growth of an H5N1 vaccine seed virus in chicken embryonated eggs. Also, the NS gene of PR8(Cambridge) enhanced the growth of an H5N1 vaccine seed virus in chicken embryonated eggs.

Figure 9:
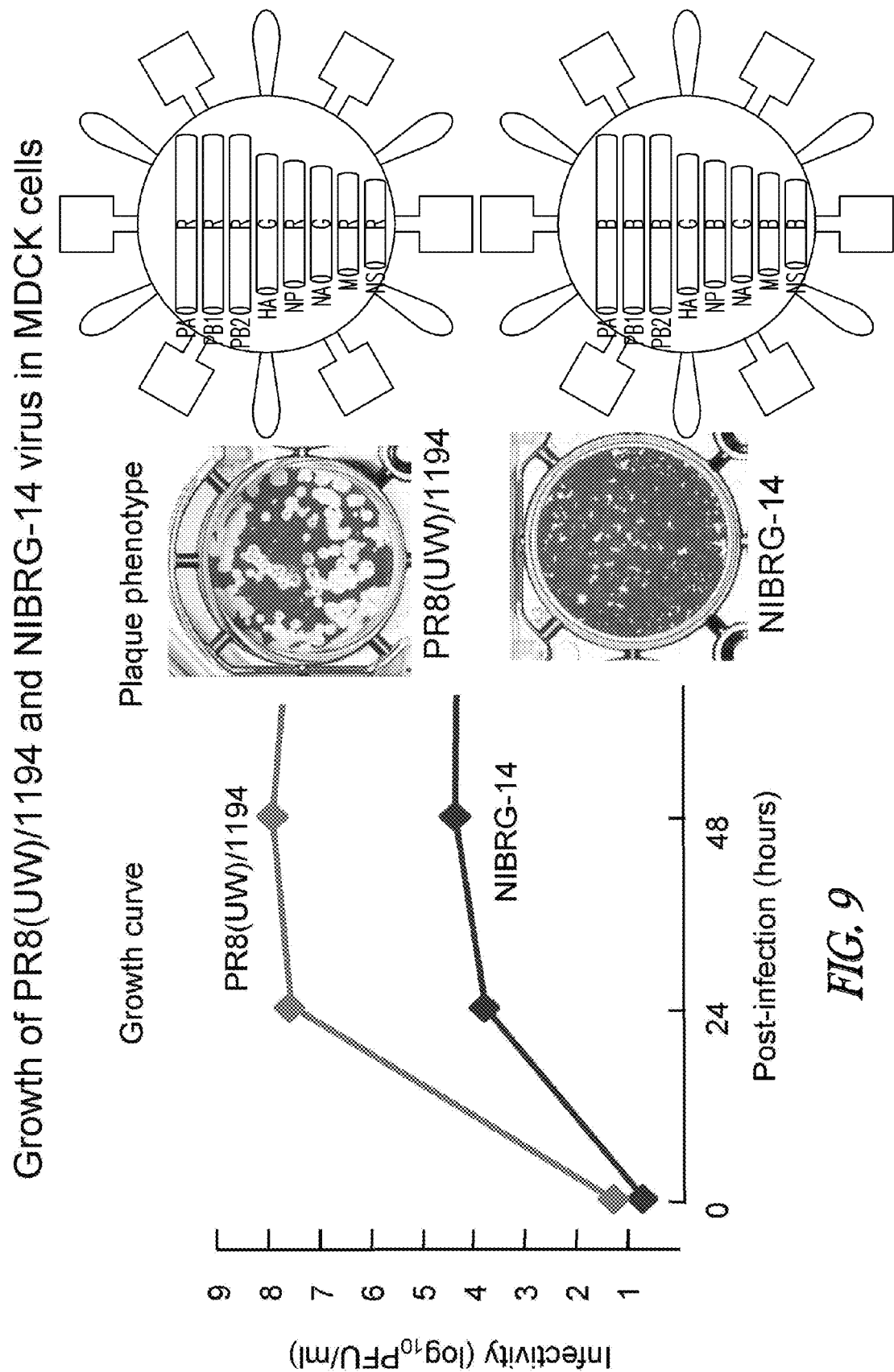
FIG. 9. Growth of PR8(UW)/1194 and NIBRG-14 virus in MDCK cells.
Figure 10:
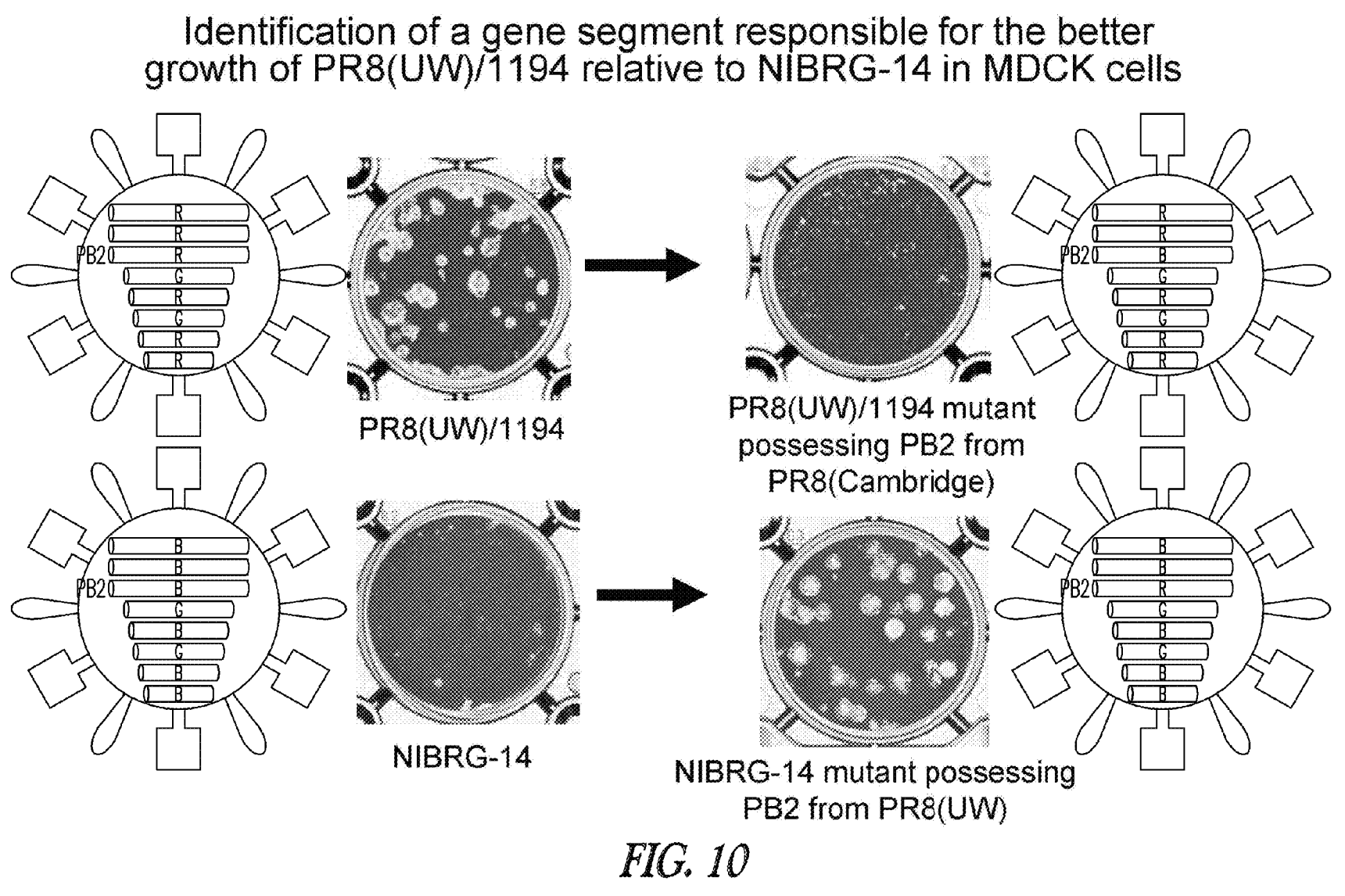
Figure 11:
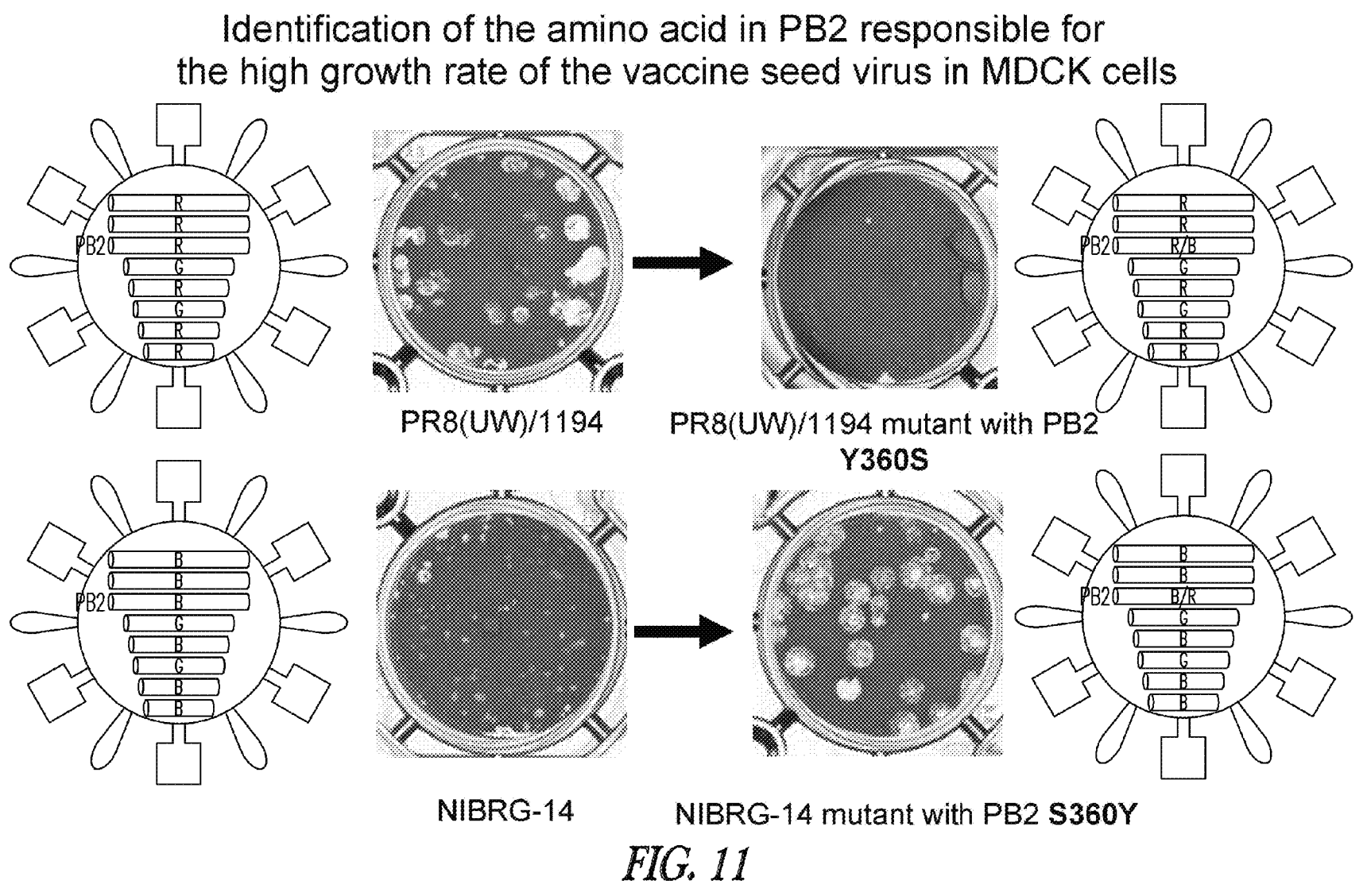

To identify the gene and amino acid(s) responsible for the high growth rate of the H5N1 vaccine seed virus in MDCK cells, the growth of PR8(UW)/1194 and NIBRG-14 virus in MDCK cells was assessed. The data in FIG. 9 show that the growth of PR8(UW)/1194 was significantly better than that of NIBRG-14 in MDCK cells. Moreover, the PB2 segment of PR8(UW) enhanced the growth of the vaccine seed virus in MDCK cells (FIG. 10). The tyrosine residue at position 360 in PB2 of PR8(UW) is likely responsible for the high growth rate of the vaccine seed virus in MDCK cells (FIG. 11).

To identify a combination of genes responsible for the high growth of an H5N1 vaccine seed virus in MDCK cells, the growth rates in MDCK cells of reassortants with different HA, NA, and NS genes was determined. NS from PR8(Cambridge) and NA with a long stalk (e.g., from A/Hong Kong/213/2003 or VN1203Fill) enhanced virus growth in MDCK cells (FIG. 12).

To determine which amino acids in NS are responsible for the high growth rate of the H5N1 vaccine seed virus in MDCK cells, the growth in MDCK cells of the H5N1 vaccine seed virus containing a heterologous NS segment was measured. An amino acid substitution from K [PR8(UW)NS] to E [PR8(Cambridge)] at position 55 of NS1 enhanced the growth of the H5N1 vaccine seed viruses in MDCK cells (FIG. 13).

FIG. 14 summarizes the genotype of an H5N1 seed virus with high growth capacity in chicken embryonated eggs or MDCK cells.

REFERENCES

Avery's Drug Treatment: Principles and Practice of Clinical Pharmacology and Therapeutics, 3rd edition, ADIS Press, Ltd., Williams and Wilkins, Baltimore, Md. (1987).
Aymard-Henry et al., Virology: A Practical Approach, Oxford IRL Press, Oxford, 119-150(1985).
Bachmeyer, Intervirology, 5:260 (1975).
Berkow et al., eds., The Merck Manual, 16th edition, Merck & Co., Rahway, N.J. (1992).
Bridgenetal., Proc. Natl. Acad. Sci. U.S.A., 93:15400 (1996).
Castrucci & Kawaoka, J. Virol., 67:759 (1993).
Castrucci et al., J. Virol., 69:2725 (1995).
Chen et al., Emerg. Infect. Dis., 10:630 (2004).
Chen et al., Vaccine, 18:3214 (2000).
Claas et al., Lancet, 351:472 (1998).
Conzelmann et al., J. Gen. Virol., 77:381 (1996).
Conzelmann et al., Trends Microbiol., 4:386 (1996).
Conzelmann, Annu. Rev. Genet., 32:123 (1998).
Cozelmann et al., J. Virol., 68:713 (1994).
Edwards, J. Infect. Dis., 169: 68 (1994).
Enami et al., Proc. Natl. Acad. Sci. U.S.A., 87:3802 (1990).
Enami et al., Virology, 185:291 (1991).
Fodor et al., J. Virol., 73:9679 (1999).
Grand and Skehel, Nature, New Biology, 238:145 (1972).
Hatta et al., Science, 293:1840 (2001).
Horimoto et al., J. Virol., 68:3120 (1994).
Horimoto et al., Vaccine, 24:3669 (2006).
Keitel et al., in Textbook of Influenza, eds. Nickolson, K. G., Webster, R. G., and Hay, A. (Blackwell, Oxford), pp. 373-390 (1998).
Kendal et al., Infect. Immunity, 29:966 (1980).
Kilbourne et al., J. Virol., 2:281 (1968).
Kilbourne, Bull. M2 World Health Org., 41: 653 (1969).
Kilbourne, Bull. World Health Org., 41:643 (1969).
Kobasa et al., Nature, 431:703 (2004).
Kovesdi et al., J. Curr. Opin. Biotechnol., 8:583 (1997).
Laver & Webster, Virology, 69:511 (1976).
Lawson et al., Proc. Natl. Acad. Sci. U.S.A., 92:4477 (1995).
Li et al., Nature, 430:209 (2004).
Marriott et al., Adv. Virus Res., 53:321 (1999).
Mizrahi, (ed.), Viral Vaccines, Wiley-Liss, New York, 39-67 (1990).
Munoz et al., Antiviral Res., 46:91 (2000).

Murphy et al., *New Engl. J. Med.*, 286:1329 (1972).
Murphy, *Infect. Dis. Clin. Pract.*, 2: 174 (1993).
Muster et al., *Proc. Natl. Acad. Sci. USA*, 88: 5177 (1991).
Nagai et al., *Microbiol. Immunol.* 43:613 (1999).
Nagai, *Rev. Med. Virol.*, 9:83 (1999).
Neumann et al., *Adv. Virus Res.*, 53:265 (1999).
Neumann et al., *J. Gen. Virol.*, 83:2635 (2002).
Neumann et al., J. Virol., 71:9690 (1997).
Neumann et al., Proc. Natl. Acad. Sci. USA, 96:9345 (1999).
Neumann et al., Virologv, 287:243 (2001).
Ogra et al., *J. Infect. Dis.*, 134: 499 (1977).
Osol (ed.), *Remington's Pharmaceutical Sciences*, Mack Publishing Co., Easton, Pa. 1324-1341 (1980).
Parks et al., *J. Virol.*, 73:3560 (1999).
Peiris et al., *Lancet*, 363:617 (2004).
Pekosz et al., *Proc. Natl. Acad. Sci. U. S. A*, 96:8804 (1999).
Radecke et al., *EMBO J.*, 14:5773 (1995).
Roberts et al., *Virology*, 247:1 (1998).
Robertson et al., *Biologicals*, 20:213 (1992).
Robertson et al., *Giornale di Igiene e Medicina Preventiva*, 29:4 (1988).
Rose, *Proc. Natl. Acad. Sci. U.S.A.*, 93:14998 (1996).
Schnell et al., *EMBO J.*, 13:4195 (1994).
Stephenson et al., *Lancet Inf Dis.*, 4:499 (2004).
Subbarao et al., *J. Virol.*, 67:7223 (1993).
Subbarao et al., *Science*, 279:393 (1998).
Subbarao et al., *Virology*, 305:192 (2003).
Sugawara et al., *Biologicals*, 30:303 (2002).
Webby & Webster et al., *Science*, 302:1519 (2003).
Webby et al., *Lancet*, 363:1099 (2004).
Wood & Robertson, *Nat. Rev. Microbiol.*, 2:842 (2004).
World Health Organization TSR No. 673 (1982).
World Health Organization. Confirmed human cases of avian influenza A (H5N1). See the URL at www.who.int/csr/disease/avian_influenza/country/en/index.html.
Xu et al., *Virology*, 261:15 (1999).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A plurality of influenza virus vectors for a reassortant, comprising a) a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising a promoter operably linked to an influenza virus NP cDNA linked to a transcription termination sequence, a vector for vRNA production comprising a promoter operably linked to an influenza virus NA cDNA linked to a transcription termination sequence, a vector for vRNA production comprising a promoter operably linked to an influenza virus M cDNA linked to a transcription termination sequence, and a vector for vRNA production comprising a promoter operably linked to an influenza virus NS cDNA linked to a transcription termination sequence, wherein the vectors for the reassortant include cDNAs for PB1, PB2, PA, NP, M, and NA with sequences that encode a polypeptide having at least 97% contiguous amino acid sequence identity to a corresponding polypeptide encoded by SEQ ID NOs:1-5 and a polypeptide having at least 90% contiguous amino acid sequence identity to a corresponding polypeptide encoded by SEQ ID NO:8, a cDNA for NS that has a Glu residue at position 55 corresponding to position 55 in SEQ ID NO:38 and encodes a polypeptide having at least 97% contiguous amino acid sequence identity to a corresponding polypeptide encoded by SEQ ID NO:6, and a cDNA for HA that is from a different influenza virus strain than a strain having gene segments with sequences corresponding to the cDNAs for PB1, PB2, PA, NP, M, NS, and NA having SEQ ID Nos. 1-6 and 8, and wherein the cDNA for PB2 has a Tyr at residue 360; and b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2, which plurality of vectors, when introduced to an avian or mammalian cell, result in production of the reassortant which is capable of enhanced replication in embryonated eggs and MDCK cells relative to a corresponding influenza virus that does not have a NA with sequences that encode polypeptide having at least 90% contiguous amino acid sequence identity to a corresponding polypeptide encoded by SEQ ID NO:8 or does not have a NS with a Glu residue at position 55 corresponding to position 55 in SEQ ID NO:38 or a PB2 with a Tyr residue at position 360.

2. The plurality of vectors of claim 1, wherein the cDNA for NS encodes a polypeptide encoded by SEQ ID NO:38.

3. The plurality of vectors of claim 1, wherein the promoter is a RNA polymerase I promoter, a RNA polymerase II promoter, a RNA polymerase III promoter, a T3 promoter or a T7 promoter.

4. The plurality of vectors of claim 1, wherein the HA is a type A HA.

5. The plurality of vectors of claim 1 wherein the HA is a type B HA.

6. The plurality of vectors of claim 1, wherein the NA is N1.

7. The plurality of vectors of claim 1, wherein the HA is H5.

8. The plurality of vectors of claim 1, wherein a plurality of the vectors of a) comprise a RNA polymerase I promoter or a RNA polymerase II promoter.

9. The plurality of vectors of claim 8, wherein the RNA polymerase I promoter is a human RNA polymerase I promoter.

10. The plurality of vectors of claim 1, wherein all of the vectors of b) comprise a RNA polymerase II promoter.

11. The plurality of vectors of claim 1, wherein each vector of a) is on a separate plasmid.

12. The plurality of vectors of claim 1, wherein each vector of b) is on a separate plasmid.

13. The plurality of vectors of claim 1, wherein the each of the vectors of b) further comprise a RNA transcription termination sequence.

14. The plurality of vectors of claim 1, wherein the HA is a chimeric HA.

15. The plurality of vectors of claim 1, wherein the cDNA for HA does not encode a polypeptide corresponding to the polypeptide encoded by SEQ ID NO:7.

16. The plurality of vectors of claim 1, wherein the NA comprises a stalk region that is greater than 20 amino acids in length.

17. The plurality of vectors of claim 1, wherein the HA is an avirulent H5 HA.

18. A method to prepare influenza virus, comprising: contacting a cell with a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising a promoter operably linked to an influenza virus NP cDNA linked to a transcription termination sequence, a vector for vRNA production comprising a promoter operably linked to an influenza virus NA cDNA linked to a transcription termination sequence, a vector for vRNA production comprising a promoter operably linked to an influenza virus M cDNA linked to a transcription termination sequence, and a vector for vRNA production comprising a promoter operably linked to an influenza virus NS cDNA linked to a transcription termination sequence, wherein the vectors for the 6:1:1reassortant include cDNAs for PB1, PB2, PA, NP, M, and NA with sequences that encode a polypeptide having at least 97% contiguous amino acid sequence identity to a corresponding polypeptide encoded by SEQ ID NOs:1-5 and a polypeptide having at least 90% amino acid sequence identity to a corresponding polypeptide having SEQ ID NO:8, a cDNA for NS that has a Glu residue at position 55 corresponding to position 55 in SEQ ID NO:38 and encodes a polypeptide having at least 97% contiguous amino acid sequence identity to a corresponding polypeptide encoded by SEQ ID NO:6, and a cDNA for HA that is from a different influenza virus strain than a strain having gene segments with sequences corresponding to the cDNAs for PB1, PB2, PA, NP, M, NS, and NA having SEQ ID Nos. 1-6 and 8, and wherein the cDNA for PB2 has a Tyr at residue 360 ; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus, wherein the infectious influenza virus has enhanced replication in embryonated eggs and MDCK cells relative to a corresponding influenza virus that does not have a NA with sequences that encode a polypeptide having at least 90% contiguous amino acid sequence identity to a corresponding polypeptide encoded by SEQ ID NO:8 or does not have a NS with a Glu residue at position 55 corresponding to position 55 in SEQ ID NO:38 or a PB2 with a Tyr residue at position 360.

19. The method of claim 18 further comprising isolating the virus.

20. Virus obtained by the method of claim 19.

21. An isolated recombinant influenza virus comprising a viral segment for PB1, PB2, PA, NP, M, and NA that has sequences for a polypeptide having at least 95% amino acid sequence identity to a corresponding polypeptide encoded by SEQ ID NOs:1-5 and at least 90% amino acid sequence identity to a corresponding polypeptide encoded by SEQ ID NO:8, a viral segment for NS with a Glu residue at position 55 corresponding to position 55 in SEQ ID NO:38 and at least 95% amino acid sequence identity to a corresponding polypeptide encoded by SEQ ID NO:6, and a viral segment for a heterologous HA, wherein the PB2 has a Tyr residue at position 360.

22. The isolated recombinant virus of claim 21, wherein the influenza virus that replicates to high titers is PR8HG.

23. The isolated recombinant influenza virus of claim 21, wherein the viral segment for HA is for H5.

24. An inactivated influenza virus vaccine comprising the isolated recombinant virus of claim 21.

25. The plurality of vectors of claim 1, wherein the cDNAs for PB1, PB2, PA, NP, and M encode a polypeptide having at least 99% contiguous amino acid sequence identity to a corresponding polypeptide encoded by SEQ ID NOs:1-5.

26. The isolated virus of claim 21, wherein the viral segments for PB1, PB2, PA, NP, and M have sequences for a polypeptide having at least 99% amino acid sequence identity to a corresponding polypeptide encoded by SEQ ID NOs:1-5.

27. An isolated recombinant influenza virus comprising a viral segment for PB1, PB2, PA, NP, M, and NS that has sequences for a polypeptide having at least 99% amino acid sequence identity to a corresponding polypeptide encoded by SEQ ID NOs:1-6, a viral segment for a heterologous HA, and a viral segment for NA, wherein the viral segment for NS encodes a NS1 protein has a Glu residue at position 55 corresponding to position 55 in SEQ ID NO:38, and wherein the viral segment for PB2 encodes a PB2 with a Tyr residue at position 360.

28. The recombinant virus of claim 27, wherein the PB1, PB2, PA, NP, and/or M have one or two substitutions relative to the corresponding polypeptide encoded by SEQ ID NOs: 1-5.

29. The recombinant virus of claim 27, wherein the NA is N1.

30. The recombinant virus of claim 27, wherein the PB1, PB2, PA, NP, and M are encoded by SEQ ID NOs:1-5.

31. The plurality of vectors of claim 1, wherein the cDNAs for PB1, PB2, PA, NP, and/or M encode a polypeptide having one or two substitutions relative to the corresponding polypeptide encoded by SEQ ID NOs:1-5.

32. The plurality of vectors of claim 1, wherein the cDNAs for PB1, PB2, PA, NP, and M encode a polypeptide encoded by SEQ ID NOs:1-5.

* * * * *

UNITED STATES PATENT AND TRADEMARK OFFICE
CERTIFICATE OF CORRECTION

PATENT NO. : 9,254,318 B2
APPLICATION NO. : 11/729557
DATED : February 9, 2016
INVENTOR(S) : Kawaoka et al.

Page 1 of 1

It is certified that error appears in the above-identified patent and that said Letters Patent is hereby corrected as shown below:

On the Title Page

Item (75), "Inventors", Column 1, Lines 2-3, delete "Madison, WI (US);" and insert --Tokyo (JP)--, therefor Item (65), "Prior Publication Data", Column 1, Line 1, after "Oct. 4, 2007", insert --¶Related U.S. Application Data (63) U.S. patent application No. 60/787,766, filed on Mar. 31, 2006.--, therefor In the Claims Column 73, Line 50, Claim 1, delete "MI," and insert --M1,--, therefor Column 75, Line 6, Claim 18, delete "360 ;" and insert --360;--, therefor Column 75, Line 20, Claim 18, delete "MI," and insert --M1,--, therefor Signed and Sealed this
Twenty-first Day of April, 2020

Andrei Iancu
*Director of the United States Patent and Trademark Office*